US007655441B2

(12) United States Patent
Otte et al.

(10) Patent No.: US 7,655,441 B2
(45) Date of Patent: *Feb. 2, 2010

(54) NUCLEIC ACID SEQUENCES HAVING GENE TRANSCRIPTION REGULATORY QUALITIES

(75) Inventors: Arie P. Otte, Amersfoort (NL); Arthur L. Kruckeberg, Shoreline, WA (US)

(73) Assignee: Chromagenics B.V., Leiden (NL)

( * ) Notice: Subject to any disclaimer, the term of this patent is extended or adjusted under 35 U.S.C. 154(b) by 439 days.

This patent is subject to a terminal disclaimer.

(21) Appl. No.: 11/580,760

(22) Filed: Oct. 13, 2006

(65) Prior Publication Data

US 2007/0031936 A1 Feb. 8, 2007

Related U.S. Application Data

(62) Division of application No. 10/190,312, filed on Jul. 5, 2002, now Pat. No. 7,192,741.

(60) Provisional application No. 60/303,199, filed on Jul. 5, 2001.

(51) Int. Cl.
| C12P 21/00 | (2006.01) |
| C12N 15/63 | (2006.01) |
| C12N 15/00 | (2006.01) |
| C12N 5/10 | (2006.01) |
| C12N 5/16 | (2006.01) |
| C07H 21/04 | (2006.01) |

(52) U.S. Cl. .................... 435/70.3; 435/320.1; 435/325; 435/358; 435/455; 536/24.1

(58) Field of Classification Search ........................ None
See application file for complete search history.

(56) References Cited

U.S. PATENT DOCUMENTS

| 5,610,053 | A | 3/1997 | Chung et al. |
| 5,773,695 | A | 6/1998 | Thompson et al. |
| 5,888,809 | A | 3/1999 | Allison |
| 5,972,605 | A | 10/1999 | Villeponteau et al. |
| 6,063,598 | A | 5/2000 | Enenkel et al. |
| 6,395,549 | B1 | 5/2002 | Tuan et al. |
| 6,413,744 | B1 * | 7/2002 | Morris et al. .............. 435/69.1 |
| 6,521,419 | B1 | 2/2003 | Koduri et al. |
| 6,586,205 | B1 | 7/2003 | Glucksmann et al. |
| 6,872,524 | B1 | 3/2005 | Otte |
| 7,192,741 | B2 | 3/2007 | Otte et al. |
| 7,267,965 | B2 | 9/2007 | Otte et al. |
| 7,364,878 | B2 * | 4/2008 | Otte et al. .............. 435/69.1 |
| 2003/0138908 | A1 | 7/2003 | Koduri et al. |
| 2003/0166042 | A1 | 9/2003 | Glucksmann et al. |
| 2003/0199468 | A1 | 10/2003 | Otte et al. |
| 2005/0106609 | A1 | 5/2005 | Otte |

FOREIGN PATENT DOCUMENTS

| EP | 1 273 666 | 1/2003 |
| WO | WO 96/04390 | 2/1996 |
| WO | WO 97/27207 | 7/1997 |
| WO | WO 98/11207 | 3/1998 |
| WO | WO 98/49289 | 11/1998 |
| WO | WO 00/05393 | 2/2000 |
| WO | WO 00/09749 | 2/2000 |
| WO | WO 00/17337 | 3/2000 |
| WO | WO 00/23606 | 4/2000 |
| WO | WO 01/59117 | 8/2001 |
| WO | WO 01/59118 | 8/2001 |
| WO | WO 02/24930 A2 | 3/2002 |
| WO | WO 03/004704 | 1/2003 |
| WO | WO 2004/055215 A1 | 7/2004 |
| WO | WO 2004/056986 A2 | 7/2004 |

OTHER PUBLICATIONS

Aranda et al., Definition of Transcriptional Pause Elements in Fission Yeast, Molecular and Cellular Biology, Feb. 1999, pp. 1251-1261, vol. 19, No. 2.
Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.
Bell et al., Insulators and Boundaries: Versatile Regulatory Elements in the Eukaryotic Genome, Science, pp. 447-450, vol. 291, No. 5503, Jan. 2001.
Burgess-Beusse et al., The insulation of genes from external enhancers and silencing chromatin, PNAS, Dec. 10, 2002, pp. 16433-16437, vol. 99, Suppl. 4.
Chan et al., p300-CBP proteins: HATs for transcriptional bridges and scaffolds, Journal of Cell Science, 2001, pp. 2363-2373, vol. 114.
Chung et al., A 5' Element of the Chicken Beta-Globin Domain Serves as an Insulator in Human Erythroid Cells and Protects against Position Effect in Drosophila, Aug. 13, 1993, Cell, pp. 505-514, vol. 74.
Database EMBL 'Online! Dec. 15, 1999, "*Homo sapiens* BAC clone RP11-572N21 from 2, complete sequence," XP002359988 retrieved from EBI accession No. EM_PRO:AC018470, database accession No. AC018470, for SEQ ID No. 17.
Database EMBL 'Online! Mar. 15, 1999, "*Homo sapiens* chromosome UNK clone CTA-435J10, working draft sequence, 1 unordered pieces," XP002359997 retrieved from EBI accession No. EM_PRO:AC007044, database accession No. AC007044 for SEQ ID No. 61.
Database EMBL 'Online! Mar. 19, 1998, CIT-HSP-2172C8.TF CIT-HSP *Homo sapiens* genomic clone 2172C8, genomic survey sequence, XP002359995 retrieved from EBI accession No. EM_PRO:B92131, database accession No. B92131 for SEQ ID No. 44.

(Continued)

*Primary Examiner*—Christopher S. F. Low
*Assistant Examiner*—Jennifer Dunston
(74) *Attorney, Agent, or Firm*—TraskBritt

(57) ABSTRACT

The invention is concerned with the systematic elucidation and identification of regulatory sequences. The invention provides among others screenings and detection methods with which regulatory sequences can be identified. The invention further provides regulatory sequences and use thereof in various fields such as, but not limited to, protein production, diagnostics, transgenic plants and animals, and the therapeutic field.

26 Claims, 20 Drawing Sheets

OTHER PUBLICATIONS

Database EMBL 'Online! Dec. 23, 1999, "Human DNA sequence from clone RP11-54H19 on chromosome 1 Contains the 3' end of the LMNA gene for lamin A/C, the gene for a novel protein similar to semaphorins (FLJ12287), a novel gene (KIAA0446), the PMF1 gene for polyamine-modulated factor 1, the BGLAP gene for bone gamma-carboxyglutamate (gla) p," XP002359989, retrived from EBI accession No. EM_PRO:AL135927, database accession No. AL135927 for SEQ ID No. 27.

Database EMBL 'Online! Sep. 24, 2000, "*Homo sapiens* chromosome 4 clone RP11-680118, working draft sequence, 25 unordered pieces," XP002359987 retrieved from EBI accession No. EM_PRO:AC080087, database accession No. AC080087 for SEQ ID No. 9.

Database EMBL 'Online! Jan. 25, 2001, "QV2-NN0045-081200-535-c10 NN0045 *Homo sapiens* cDNA, mRNA sequence." XP002359993 retrieved from EBI accession No. EM_PRO:BF960930, database accession No. BF960930 for SEQ ID No. 43.

Database EMBL 'Online! Apr. 26, 2001, "RST28606 Athersys RAGE Library *Homo sapiens* cDNA, mRNA sequence," XP002359993 retrieved from EBI accession No. EM_PRO:BG209092, database accession No. BG209092 for SEQ ID No. 40.

Database EMBL 'Online! Oct. 28, 1998, "*Homo sapiens* neurexin III-alpha gene, partial cds," XP002359992, retrieved from EBI accession No. EM_PRO:AF099810, database accession No. AF099810 for SEQ ID No. 43.

Database EMBL 'Online! Sep. 29, 1999, "*Homo sapiens* genomic DNA, chromosome 22q11.2, Cat Eye Syndrome region, clone:N64E9," XP002359991, retrieved from EBI accession No. EM_PRO:AP000526, database accession No. AP000526 for SEQ ID No. 40.

Database EMBL 'Online! Sep. 29, 1999, *Homo sapiens* genomic DNA, chromosome 22q11.2, Cat Eye Syndrome region, clone:N14H11, XP002359994 retrieved from EBI accession No. EM_PRO:AP000525, database accession No. AP000525 for SEQ ID No. 44.

Database EMBL 'Online! Sep. 29, 1999, "*Homo sapiens* genomic DNA, chromosome 22q11.2, Cat Eye Syndrome region, clone:c91G6," XP002359996 retrieved from EBI accession No. EM_PRO:AP000528, database accession No. AP000528 for SEQ ID No. 45.

Database EMBL 'Online! Feb. 3, 2004, "Sequence 33099 from Patent W002068579," XP002359986 retrieved from EBI accession No. EM_PRO:CQ747165, database accession No. CQ747165 for SEQ ID No. 9.

Database EMBL 'Online! Aug. 4, 1999, "*Homo sapiens* chromosome 19 clone CTD-2540B15, complete sequence," XP002359985 retrieved from EBI accession No. EM_PRO:AC008738, database accession No. AC008738 for SEQ ID No. 7.

Database EMBL 'Online!, Jul. 8, 1992, *H. sapiens* HOX4B gene upstream sequence XP002348163 retrieved from EBI, Database accession No. X67079, Abstract.

Eggermont et al., Poly(A) signals and transcriptional pause sites combine to prevent interference between RNA polymerase II promoters, The EMBO Journal, 1993, pp. 2539-2548, vol. 12, No. 6.

Emery et al., "A chromatin insulator protects retrovirus vectors from chromosomal postion effects," Proceedings of the National Academy of Sciences of USA, Aug. 1, 2000, pp. 9150-9155, vol. 97, No. 16.

European Search Report dated Dec. 22, 2005, for EP 05 07 6209.

Farrell et al., Conserved CTCF Insulator Elements Flank the Mouse and Human Beta-Globin Loci, Molecular and Cellular Biology, Jun. 2002, pp. 3820-3831, vol. 22. No. 11.

Frengen et al., Modular bacterial artificial chromosome vectors for transfer of large inserts into mammalian cells, Genomics. vol. 68, No. 2, pp. 118-126, Sep. 2000.

GenBank Accession No. AC007689. 13, GI: 8573011, Jun. 25, 2000.

GenBank Accession No. AL096766. 12, GI: 5738627, Aug. 17, 1999.

Glucksmann et al., Database accession No. AAH76193, Oct. 29, 2001.

Han et al., "Matrix attachment regions (MARs) enhance transformation frequency and transgene expression in poplar," Transgenic Research, 1997, pp. 415-420, vol. 6.

Johnson et al., Requirements for utilization of CREB binding protein by hypersensitive site two of the Beta-globin locus control region, Nucleic Acids Research 2002, pp. 1522-1530, vol. 30, No. 7.

Kellum et al., A Group of scs Elements Function as Domain Boundaries in an Enhancer-Blocking Assay, Molecular and Cellular Biology, May 1992, pp. 2424-2431, vol. 12, No. 5.

Kwaks et al., Identification of anti-repressor elements that confer high and stable protein production in mammalian cells, Nature Biotechnology, May 20, 2003, pp. 553-558, vol. 21, No. 5.

Maniatis et al., Recognition Sequences of Repressor and Polymerase in the Operators of Bacteriophage Lambda, Cell, Jun. 1975, pp. 109-113, vol. 5.

Martinez-Balbas et al., The acetyltransferase activity of CBP stimulates transcription, The EMBO Journal, 1998, pp. 2886-2893, vol. 17, No. 10.

Mielke et al., "Stabilized, long-term expression of heterodimeric proteins from tricistronic mRNA," Gene, Aug. 22, 2000, pp. 1-8, vol. 254, No. 1-2.

Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.

Partial European Search Report, EP 05 07 6209, dated Oct. 7, 2005.

Pile et al., "GAGA Factor-dependent Transcription and Establishment of DNase Hypersensitivity Are Independent and Unrealated Events In Vivo," J. of Biological Chemistry, Jan. 14, 2000, pp. 1398-1404, vol. 275, No. 2.

Reik et al., Biotechnologies and therapeutics: Chromatin as a target, Current Opinion in Genetics & Development, 2002, pp. 233-242, vol. 12.

Seum et al., A GAL4-HP1 fusion protein targeted near heterochromatin promotes gene silencing, Chromosoma, 2000, pp. 453-459, vol. 109.

Shizuya et al., Cloning and stable maintenance of 300-kilobase-pair fragments of human DNA in *Escherichia coli* using an F-factor-based-vector. Proc Natl Acad Sci USA. vol. 89, No. 18, pp. 8794-8797, Sep. 1992.

Sigrist et al., "Chromatin Insulator Elements Black the Silencing of a Target Gene by the Drosophila Polycomb Response Element (PRE) but Allow trans Interactions Between PREs on Different Chromosomes," Genetics, Sep. 1997, pp. 209-211, vol. 147, No. 1.

Van Der Vlag et al., Transcription Repression Mediated by Polycomb Group Proteins and Other Chromatin-associated Repressors Is Selectively Blocked by Insulators, Journal of Biological Chemistry, Jan. 7, 2000, pp. 697-704, vol. 275, No. 1.

West et al., "Insulators: many functions, many mechanisms," Genes and Development, Feb. 1, 2002, pp. 271-288, vol. 16, No. 3.

PCT International Search Report, PCT/NL02/00390, dated Jul. 29, 2003.

Office Action for U.S. Appl. No. 11/580,619, dated Mar. 23, 2009.
Office Action for U.S. Appl. No. 11/580,494, dated Mar. 23, 2009.
Office Action for U.S. Appl. No. 11/580,644, dated Mar. 20, 2009.
Office Action for U.S. Appl. No. 11/580,604, dated Mar. 20, 2009.
Office Action for U.S. Appl. No. 11/580,620, dated Mar. 23, 2009.
Office Action for U.S. Appl. No. 11/580,605, dated Mar. 20, 2009.

* cited by examiner

Vector for testing STAR activity

FIG. 9

STAR finemapping

| | | Growth |
|---|---|---|
| STAR10 | ▬▬▬▬▬▬ | ++ |
| 10A | ▬▬ | +++ |
| 10B | ▬▬ | - |
| 10C | ▬▬ | - |
| STAR27 | ▬▬▬▬▬▬▬ | + |
| 27A | ▬▬ | - |
| 27B | ▬▬ | +/- |
| 27C | ▬▬ | - |

FIG. 12
STAR element orientation
A. pSelect vector with cloned STAR element:
B. pSDH vector, STARs in native orientation:
C. pSDH vector, STARs in opposite orientation:

STAR copy number dependency

Schematic diagram of Enhancer and Enhancer-blocking Assays

STAR18 sequence and function is conserved between mouse and human

FIG. 20

```
SEQ ID:45
>STAR45
CACGCCCCAGCGTGCCCTGGACTACTGCTCCGCAGGACTCCTGTTCTGCTGCACCCTGGACTACGGCACCAGAGGACCCAG
CTCCCGCCGGCCTGAGCTATGGCACCAGAGGACCCAGCTCCCGGCAGCCTGGACTATGGCACCAGAGGACCCAGCCCCCCG
CTTCCTGGGCTAAGGCACAGTAGGACCCTGCCTCATCGTGTACTCCTGCTCAGGAGGACCCTCGCAGGGCGGCGCACTGGA
CTAAGCTACTGAAGGAGCCCCACCCCTGCCTAACCCTGGACTAAGGCACTGGAGAACTCTTGCTCCGCAGAGCCACGGACT
CTTGCACAAGAGAACCTCAGCCCAGCCGTGCCCTGGACTGTGGCACAGTAGGGCCCACACCACGCCATGGACTCCTGTATT
GGAGGAAGAGTAGTGATAAATGTCCAGGTTTACAACTTGAAAAGTAGCAATCAATGTGCCACAATAGATGGATGTGATGTA
AAATTATAAATGATGAAAACATTATGTGTAATTGCCTAGCCAGAACAGTTACACAAGACAAAGACGTAAAAGAAATCCACA
TAGGGAAGGAAGAGGTAAGATTGTTTCTGTTTTTTGAAAATATAATCTTAAGATAGAGAAAATCTTAAAGATTCCACCAAA
ATAAATGGTTATAGCTGATGAAGAAATTCAATAAAGTTAATAGTTACAAAATCAACATACAAATATCATTATTGTTTCTAT
TAACTAATGACAAACTATTACCTGAAAAATAAAGGCAATTCAATTTATAATAGAATCAAAACAGATATATAAATATATAAA
AGACAGGAGTAAATTTAATCAAAACCATAAAAGATTTACATACTGAAAACTATAGCACATTGATGAAAAAAATTAAAATGG
CATAAATAAATGGAGAAACATCCTTCATTGATGGATTCAAAAATTAGTATTGTAAAAGTGTCAATGCTACCCAAAGCAATC
TACAGATTAAATGCAACCACTATCAAATTCCAATGTCATTCTTCACAGAAATAGAAAAATTACTGCTAAAATTTGTATGGA
ACCACAAAAGACCTGGACCAACCAAAGCAATCTTGAACAAAAAGAACAAAGCTGGAGGCATCAGACTACCTGACTCCAAAC
TCTATTACAAAGCTATAGGAATTAAAACAGCATAGCAATGGCATAAAAACAGACATGTAAAACAGTACAAAGGGATATAGA
ACCTGTAAATAAATCCGTGTGTCTGTGGTCAATTGATTTTTTGATAAAATAACTAAAAATACACAGTGAAGAAAGAAAATT
ATTTTCAATAAATGGTGTAGACAAAACTGACTATCCACATACAGAAGAATAAAATTTGACTTTTATTTTGCTCTTTATACA
AGCATCAAATCAAAATTAAAGTTTAAATGTAAAACTACTACAAGGAAATATAGAAGGAGACTGTATGACATTGGCCTGAGC
TATGATTTTCTGTAGATTATTCCAAAAGGCAACAAAAGCAAAACACACAAATGAGACTGCATAAAACTTAAAACTTTTCCA
CAGGAAAAGAAGCAATGATAGAATTAAGAGAACCCACAAATGGGATAATATTTTAAACCATACATCAGGTAAGGGGCTCA
TATAATAATATATAAGCAACTCAACCTACTCAAAAATAAGAAAAAAACTATGCTTATTAAAAAATAAGCAAAGAATCAGAA
TAGACATTTCCTACATCATACAAAAGGCCAACCAGGTACATGAAAAAATCATAAACATTCCTAATTATCAGAGAAGTGCAA
ATCAATGCCACAATGAGATATCACCTCACACATTTTACTAGGGCTATTATAAAAAAAGATGGAAGATAAGTGTTGGTGAGG
ATGTGGAGAAAAAGAAACCCTGTACACTGTTGGTAGGAATGGAAATTAGTACAGCCATCTTGGAAAACAGTACGAAGCTTT
CTCAAGAAATTATAAATTTATTTACCCTATGATCCAT
``` ns having become avail
NUCLEIC ACID SEQUENCES HAVING GENE TRANSCRIPTION REGULATORY QUALITIES

CROSS-REFERENCE TO RELATED APPLICATION

This application is a divisional of patent application Ser. No. 10/190,312, filed Jul. 5, 2002, now U.S. Pat. No. 7,192,741, which application claims priority under 35 U.S.C. § 119(e) to U.S. Provisional Patent Application Ser. No. 60/303,199, filed on Jul. 5, 2001, the contents of both of which are incorporated by this reference.

STATEMENT ACCORDING TO 37 C.F.R. § 1.52(e)(5)—SEQUENCE LISTING SUBMITTED ON COMPACT DISC

Pursuant to 37 C.F.R. § 1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing.txt" which is 531 KB and created on Jan. 9, 2003.

TECHNICAL FIELD

The invention relates to the fields of medicine and cellular biology. The invention in particular relates to means and methods for regulation of gene transcription. The invention further relates to means and methods for determining whether a DNA sequence comprises a gene transcription modulating quality and/or a gene transcription repressing quality.

BACKGROUND

With the progression of the various genome projects, sequences of entire organismal genomes have become available. The flood of data has raised the interest of many investigators. One of the more noticeable discoveries was the observation that the human genome does not code for significantly more genes than the genome of simple organisms like the fruit fly. The focus of many investigators is now shifting from the identification of genes to the determination of gene expression and gene function. Examples of such technologies are DNA microarrays, functional genomics applications and proteomics. These technologies have in common that they are centered about the function and expression of coding sequences. However, while our knowledge of genes increases dramatically, the understanding of how the expression of the genes is regulated is limiting the ability to apply this rapidly increasing knowledge. This is, for instance, the case in the generation of transgenic plants and animals and in human gene therapy. In these applications, foreign nucleic acid is typically introduced into cells to obtain expression of coding sequences. Often, integration of the foreign nucleic acid into the cell's genome is required for prolonged function of the introduced sequences. However, integration of sequences into the genome can lead to unpredictability of expression because, among other things, the surrounding DNA influences the transcription of the integrated sequences. This unpredictability is in part due to the fact that introduced sequences cannot be provided yet with sufficient genetic information to functionally isolate the integrated sequences from the transcription influencing effects of the surrounding DNA. In another part, this is due to the fact that not enough is known about the transcription influencing effects of surrounding DNA.

SUMMARY OF THE INVENTION

Described are DNA sequences that have a capacity to influence transcription of genes in cis. Typically, although not necessarily, the investigated sequences do not code by themselves for a functional protein. Various sequence elements with the capacity to affect gene transcription in cis, have been identified. These elements range from promoters, enhancers, and silencers to boundary elements and matrix attachment regions.

The fact that so many different types of regulatory sequences have been discovered gives the impression that it is very easy to design effective expression cassettes. However, quite the contrary is true. Designing expression cassettes is still often driven by trial and error. It is quite often possible to obtain some kind of expression of a foreign gene in a target cell or its progeny. However, very often it is difficult to predict with any kind of accuracy the level of expression or the persistence of expression that an expression cassette can display in a target cell.

Provided are, among other things, means and methods for detecting and isolating new transcription regulatory elements. A method of detecting, and optionally selecting, a DNA sequence with a gene transcription-modulating quality is provided, comprising providing a transcription system with a variety of a fragment-comprising vectors, the vectors comprising i) an element with a gene-transcription repressing quality, and ii) a promoter directing transcription of a reporter gene, the method further comprising performing a selection step in the transcription system in order to identify the DNA sequence with the gene transcription modulating quality. In certain embodiments, the fragments are located between i) the element with a gene-transcription repressing quality, and ii) the promoter directing transcription of the reporter gene. RNA polymerase initiates the transcription process after binding to a specific sequence, called the promoter, which signals where RNA synthesis should begin. A modulating quality can enhance transcription from the promoter in cis, in a given cell type and/or a given promoter. The same DNA sequence can comprise an enhancing quality in one type of cell or with one type of promoter, whereas it can comprise another or no gene transcription modulating quality in another cell or with another type of promoter. Transcription can be influenced through a direct effect of the regulatory element (or the protein(s) binding to it) on the transcription of a particular promoter. Transcription can however, also be influenced by an indirect effect, for instance because the regulatory element affects the function of one or more other regulatory elements. A gene transcription modulating quality can also comprise a stable gene transcription quality. With stable is meant that the observed transcription level is not significantly changed over at least 30 cell divisions. A stable quality is useful in situations wherein expression characteristics should be predictable over many cell divisions. Typical examples are cell lines transfected with foreign genes. Other examples are transgenic animals and plants and gene therapies. Very often, introduced expression cassettes function differently after increasing numbers of cell divisions or plant or animal generations. In certain embodiments, a stable quality comprises a capacity to maintain gene transcription in subsequent generations of a transgenic plant or animal. Of course in case expression is inducible the quality comprises the quality to maintain inducibility of expression in subsequent generations of a transgenic plant or animal. Frequently, expression levels drop dramatically with increasing numbers of cell divisions. With a method described herein it is possible to detect and optionally select a DNA sequence that is capable of, at least in part, preventing the dramatic drop in transcription levels with increasing numbers of cell divisions. Thus, in one embodiment, the gene transcription modulating quality comprises a stable gene transcription quality. Strikingly, fragments comprising a DNA sequence with the stable gene transcription quality can be detected and optionally selected with a method of the invention, in spite of the fact that the method does not necessarily measure long term stability of transcription. In one embodiment, the gene transcription modulating quality comprises a stable gene transcription enhancing quality. It has been observed that incorporation of a DNA sequence with a gene transcription modulating quality in an expression vector with a gene of interest, results in a higher level of transcription of the gene of interest, upon integration of the expression vector in the genome of a cell and moreover that the higher gene expression level is also more stable than in the absence of the DNA sequence with a gene transcription modulating quality.

BRIEF DESCRIPTION OF THE DRAWINGS

FIG. 9. Minimal essential sequences of STAR10 and STAR27. Portions of the STAR elements were amplified by PCR: STAR10 was amplified with primers E23 and E12 to yield fragment 10A, E13 and E14 to yield fragment 10B, and E15 and E16 to yield fragment 10C. STAR27 was amplified with primers E17 and E18 to yield fragment 27A, E19 and E20 to yield fragment 27B, and E21 and E22 to yield fragment 27C. These sub-fragments were cloned into the pSelect vector. After transfection into U-2 OS/Tet-Off/LexA-HP1 cells, the growth of the cultures in the presence of Zeocin was monitored. Growth rates varied from vigorous (+++) to poor (+/−), while some cultures failed to survive Zeocin treatment (−) due to absence of STAR activity in the DNA fragment tested.

FIG. 12. Schematic diagram of the orientation of STAR elements as they are cloned in the pSelect vector (panel A), as they are cloned into pSDH vectors to preserve their native orientation (panel B), and as they are cloned into pSDH vector in the opposite orientation (panel C).

FIG. 20. STAR 45 sequence (SEQ ID NO: 45)

DETAILED DESCRIPTION OF THE INVENTION

Figure 1:
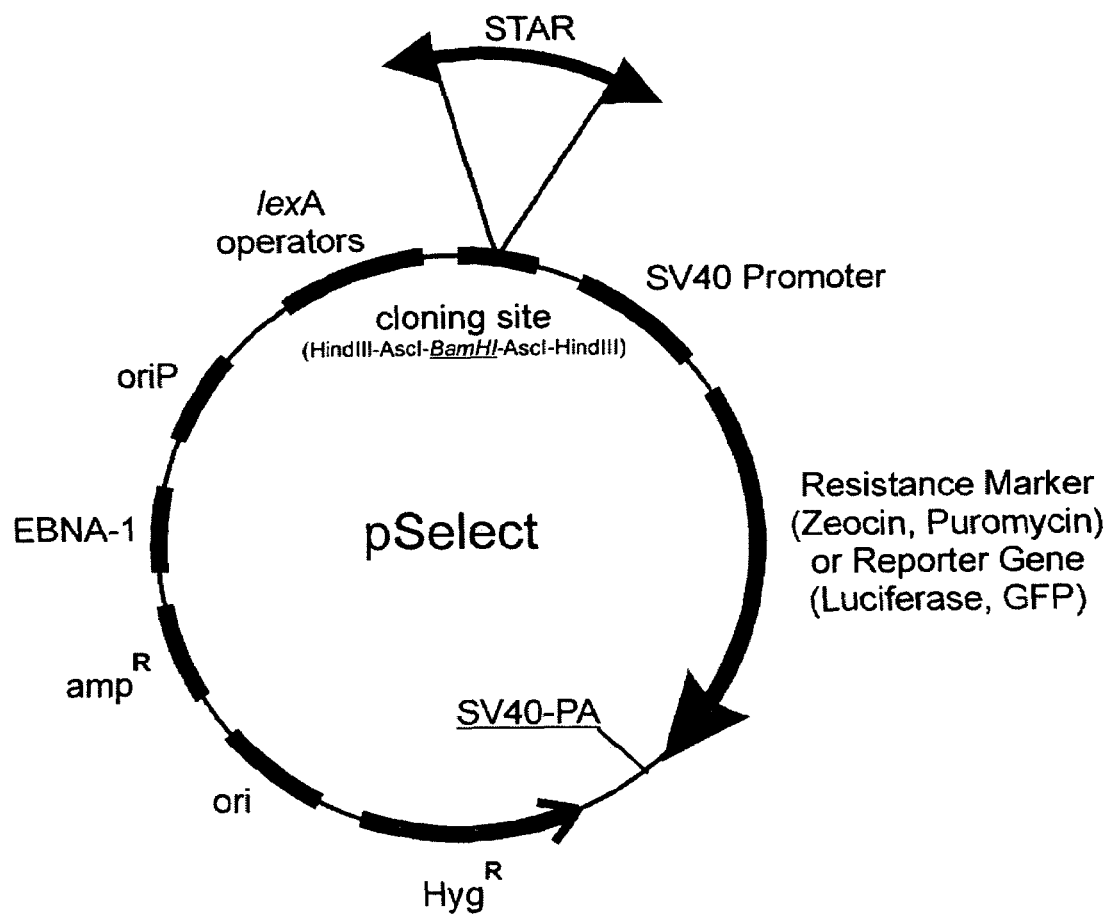
FIG. 1. The pSelect family of plasmids for selecting and characterizing STAR elements. A resistance marker (Zeocin or puromycin) or reporter gene (GFP or luciferase) under control of the promiscuous SV40 promoter is adjacent to a BamHI cloning site flanked by AscI and HindIII sites. Upstream of the cloning site are lexA operators to which lexA protein can bind. Binding of chimeric lexA-Polycomb group proteins to the operators causes repression of the marker or reporter gene. DNA fragments inserted at the cloning site that block repression are identified by the persistent expression of the marker or reporter gene. The plasmid replicates episomally in cultured mammalian cells due to the oriP sequence.

In experiments designed to introduce a gene of interest into the genome of a cell and to obtain expression of the gene of interest, the following has been observed. If together with the gene of interest also a DNA sequence with a gene transcription modulating quality was introduced, more clones could be detected that expressed more than a certain amount of gene product of the gene of interest, than when the DNA sequence was not introduced together with the gene of interest. Thus the present invention also provides a method for increasing the number of cells expressing a more than a certain level of a gene product of a gene of interest upon providing the gene of interest to the genome of the cells, comprising providing the cell with a DNA sequence comprising a gene transcription modulating quality together with the gene of interest.

The chances of detecting a fragment with a gene transcription-modulating quality vary with the source from which the fragments are derived. Typically, there is no prior knowledge of the presence or absence of fragments with the quality. In those situations many fragments will not comprise a DNA sequence with a gene transcription-modulating quality. In these situations a formal selection step for DNA sequences with the quality is introduced. This is done by selection vectors comprising the sequence on the basis of a feature of a product of the reporter gene, which can be selected for or against. For instance, the gene product may induce fluorescence or a color deposit (e.g., green fluorescent protein and derivatives, luciferase, or alkaline phosphatase) or confer antibiotic resistance or induce apoptosis and cell death.

A method of the invention is particularly suited for detecting and optionally selecting a DNA sequence comprising a gene transcription-enhancing quality. It has been observed that at least some of the selected DNA sequences, when incorporated into an expression vector comprising a gene of interest, can dramatically increase gene transcription of the gene of interest in a host cell even when the vector does not comprise an element with a gene-transcription repressing quality. This gene transcription enhancing quality is very useful in cell lines transfected with foreign genes or in transgenic animals and plants.

As used herein, the transcription system comprises host cells. Using host cells warrants that fragments are detected and optionally selected with activity in cells.

An element with a gene transcription repressing quality will, in a method of the invention, repress transcription from a promoter in the transcription system used. The repression does not have to lead to undetectable expression levels. Important is that the difference in expression levels in the absence or presence of repression is detectable and optionally selectable. In certain embodiments, gene-transcription repression in the vectors results in gene-transcription repressing chromatin. In these embodiments, DNA sequences can be detected, and optionally selected that are capable of at least in part counteracting the formation of gene-transcription repressing chromatin. In one aspect, a DNA sequence capable of at least in part counteracting the formation of gene-transcription repressing chromatin comprises a stable gene transcription quality. In certain embodiments, the DNA sequence involved in gene-transcription repression is a DNA sequence that is recognized by a protein complex and wherein the transcription system comprises the complex. Preferably the complex comprises a heterochromatin-binding protein comprising HP1, a Polycomb-group (Pc-G) protein, a histone deacetylase activity or MeCP2 (methyl-CpG-binding protein). Many organisms comprise one or more of these proteins. These proteins frequently exhibit activity in other species as well. The complex can thus also comprise proteins from two or more species. The mentioned set of known chromatin-associated protein complexes is able to convey long-range repression over many base pairs. The complexes are also involved in stably transferring the repressed status of genes to daughter cells upon cell division. Sequences selected in this way are able to convey long-range anti-repression over many base pairs (van der Vlag et al., 2000).

The vector used can be any vector that is suitable for cloning DNA and that can be used in a transcription system. When host cells are used it is preferred that the vector is an episomally replicating vector. In this way, effects due to different sites of integration of the vector are avoided. DNA elements flanking the vector at the site of integration can have effects on the level of transcription of the promoter and thereby mimic effects of fragments comprising DNA sequences with a gene transcription modulating quality. In certain embodiments, the vector comprises a replication origin from the Epstein-Barr virus (EBV), OriP, and a nuclear antigen (EBNA-1). Such vectors are capable of replicating in many types of eukaryotic cells and assemble into chromatin under appropriate conditions.

In another aspect the invention provides a DNA sequence comprising i) a DNA sequence isolated from a plant or vertebrate, or derivatives thereof, or ii) a synthetic DNA sequence or one constructed by means of genetic engineering, which DNA sequence is a repression-inhibiting sequence which, by the method according to the present invention can be detected, selected and optionally cloned. In another aspect, provided is a DNA sequence comprising i) a DNA sequence isolated from a plant or vertebrate, or derivatives thereof, or ii) a synthetic DNA sequence or one constructed by means of genetic engineering, which DNA sequence is detected, selected and optionally cloned by means of the method of the invention. Preferably the DNA sequence comprises a sequence as depicted in Table 3 or a functional homologue thereof. A functional homologue of a sequence as depicted in Table 3 is a sequence derived with the information given in Table 3. For instance, a sequence that can be derived from a sequence in Table 3 by deleting, modifying and/or inserting bases in or from a sequence listed in Table 3, wherein the derived sequence comprises the same activity in kind, not necessarily in amount, of a sequence as depicted in Table 3. A functional homologue is further a sequence comprising a part from two or more sequences depicted in Table 3. A synthetic DNA sequence is a sequence that is not derived directly or indirectly from a sequence present in an organism. For instance, a sequence comprising a drosophila scs or scs' sequence is not a synthetic sequence, even when the scs or scs' sequence was artificially generated.

In one aspect, the invention is concerned with increasing knowledge of higher order gene regulation and with means and methods for utilizing this knowledge. Whereas elements, such as classical promoters and enhancers, have been characterized that direct and regulate transcription of single genes, higher order regulatory elements that govern the gene transcription capabilities of entire chromosome regions have as yet received little attention. Much of our knowledge regarding such higher order elements comes from the study of embryogenesis. During embryogenesis, cells become committed to different developmental pathways. Once committed, cells rarely change their fates, even after many cell divisions.

The stable transmission of cell type specific gene transcription patterns is generally not dependent on the context of a promoter, but is instead mediated by changes in the structure of the DNA and associated proteins, termed chromatin. Gene regulation at the chromosomal level involves modifications of DNA (e.g., methylation), histones, (e.g., acetylation and/or methylation), and long-range interactions between distant chromosomal elements.

The chromatin template is a highly condensed complex of DNA, histones, and non-histone proteins, which is able to package the entire genome into the nucleus and simultaneously allow the appropriate transcription of specific genes. The eukaryotic chromosome is not a uniform template for the activation of gene transcription. Different types of chromatin and chromatin regions can be distinguished, which differentially affect gene transcription. The so-called heterochromatin regions identify "closed" chromatin structures whereas euchromatin is associated with a more diffuse and "open" chromatin structure. The euchromatin region can be subject to structural changes, resulting in more or less condensed structures, referred to as facultative heterochromatin and euchromatin. The formation of facultative euchromatin or heterochromatin is believed to represent the underlying mechanism of chromatin-mediated gene regulation, keeping genes in an active or a repressed state, in a cell type specific manner.

In all eukaryotes several chromatin-associated protein complexes have been identified that are involved in the maintenance of cell type specificity, one of which is the Polycomb group (PcG) complex. The PcG complex is involved in the stable repression of genes, in which changes in chromatin structure are believed to play an important role. Similarly, a second class of proteins, named the trithorax group (TrG), has been identified that counteracts the action of the PcG proteins. TrG proteins are involved in the maintenance of gene transcription. Based on their respective modes of action, PcG and TrG proteins therefore represent a cellular memory system that is important for the heritable transmission of gene transcription patterns.

How PcG and TrG complexes are associated with their target genes is still unclear. Genetic studies have characterized cis-acting regulatory sequences that maintain transcriptionally inactive states of genes. The silencing mediated by these cis-acting regulatory sequences is dependent on the presence of functional PcG proteins, and hence these sequences have been termed PcG response elements (PREs). Sequences have been identified that are involved in PcG mediated repression of chromatin. As yet however, (in both vertebrates and plants) complete PREs comprising all sequence information required to mediate repression of chromatin have not been found.

A Polycomb-group response element is an element that is capable of repressing the transcription from a promoter in response to the direct and/or indirect interaction of one or more Polycomb group proteins with the element. A polycomb-group-like response element is a Polycomb-group response element or alternatively it is an element capable of repressing the transcription of a promoter upon the direct and/or indirect interaction of one or more proteins with the element, wherein the one or more proteins do not belong to the Polycomb-group, but wherein as a result of the interaction gene transcription repressing chromatin is formed. Examples of such proteins are chromatin-associated proteins such as heterochromatin protein1 (HP1) (Eisenberg et al., 1990). Another chromatin-associated protein that represses gene activity is methyl-CpG-binding protein, MeCP2 (Nan et al., 1997). In certain embodiments, a polycomb-group-like responsive element of the invention comprises the capacity to repress transcription of a promoter over long distances, preferably over more than 2000 base pairs (van der Vlag et al., 2000).

A reporter gene is a gene encoding an expression product of which the presence can be detected directly or indirectly in a cell.

Examples of DNA sequences with a gene transcription modulating quality are the so-called STAR elements listed in Tables 1 and 2.

Methods of the invention result in the cloning and identification of a number of elements comprising a gene transcription modulating quality. Such an element may contain irrelevant nucleic acid that is not instrumental in performing the quality, for instance not involved in the formation of gene-transcription repressing chromatin. Functional sequences in such elements can be delineated by various methods known in the art. In one embodiment deletions and/or substitutions are made in a DNA sequence with a gene transcription modulating quality. DNA that is modified in such a way, is tested for activity in a method of the invention. This can be done using a single modified nucleic acid or by generating a collection of test nucleic acids comprising the modified nucleic acid. Elucidation of functional sequences within DNA sequences of the invention enables the elucidation of consensus sequences for elements with a gene transcription modulating quality. It is anticipated that more than one type of consensus sequence is found for an element comprising a gene transcription modulating quality. The invention thus further provides a library of isolated and/or recombinant nucleic acids comprising gene transcription modulating and/or gene transcription repressing qualities such as polycomb-group-like response elements. In one embodiment the library comprises isolated and/or recombinant nucleic acids comprising the same consensus sequence. In certain embodiments, the library comprises more than one type of consensus sequence. The library can be used for instance for determining whether a given DNA molecule comprises a DNA modulating quality. In certain embodiments, the library comprises essentially all elements with a gene transcription enhancing function, elements comprising a stable gene transcription quality and/or elements with a gene transcription repressing quality such as polycomb-group-like response elements, of a chromosome. Together with knowledge on the location of these elements on a chromosome this allows a person skilled in the art to generate a prediction for higher order regulation of gene expression of genes naturally present on the chromosome and for genes (foreign nucleic acid) introduced into the chromosome by recombinant means. Such a prediction can be used for example to select a suitable candidate location on the chromosome for the insertion of foreign DNA. A suitable location can be a location expected to be specifically expressed in a certain cell, cell type and/or tissue. Preferably, the chromosome comprises chromosome 21 or chromosome 22. In a particularly preferred embodiment all DNA sequences comprising a gene transcription modulating or a gene transcription repressing quality in a cell, are in the library. In this embodiment the entire genome can be used for the prediction of a suitable candidate location. In one embodiment the library has been generated in different cell lines of species ranging from plants to human. In different cell lines and/or species different proteins (or protein complexes) capable of interacting with DNA sequences with a gene transcription repressing quality, will be expressed, resulting in different DNA elements with a gene transcription repressing quality. Similarly different proteins that interact directly or indirectly with DNA sequences comprising a gene transcription modulating quality will be expressed. Therefore the make-up of the library is cell-type dependent and dependent on the presence of the relevant proteins. This is also the case with polycomb-group-like response elements. If HP1 is expressed in cell type one, elements depending on HP1 will be detected by method of invention. If HP1 is not expressed in cell type two, method of invention will not detect the element that has been retrieved from cell type one.

In one aspect, the library comprises at least one element capable of at least in part counteracting the formation of gene-transcription repressing chromatin. Together with knowledge of the location of DNA sequences with a gene transcription repressing quality on a chromosome or genome, knowledge of the location of such counteracting elements allows more accurate prediction of higher order regulation of gene transcription of (inserted) genes in the chromosome or genome. The library may further comprise other transcription regulatory elements such as enhancers and silencers. Although such sequences have limited influence on higher order gene regulation, information on the location of such other sequences further increases the accuracy of the prediction on suitable locations in the genome for the expression of foreign sequences introduced therein. The library may include essentially all DNA sequences comprising a gene transcription modulating quality and/or all other regulatory sequences of a chromosome.

Considering that already a chromosome typically consists of several tens of millions of bases, it is preferred that the information that the library can give on higher order gene regulation is incorporated into an at least partially automated system.

Another use of a library is the generation of a prediction on transcription of genes upon targeted modification of sequences on a chromosome such that "higher order" regulatory sequences are mutated. For instance, one or more polycomb-group-like responsive elements of the invention, and/or other regulatory elements on the chromosome can be mutated. This is expected to change the transcription levels of the genes that are in the vicinity of the polycomb-group-like responsive elements and/or. other expression modulating elements.

Yet another use of a library or system is the prediction of gene expression resulting from mutations in the genome. In cases where a mutation results in altered gene transcription, detection of such altered gene transcription can indicate the presence of the naturally occurring mutation. This approach is useful for instance in limiting the number of sequences or proteins to be tested in a diagnostic assay. This is particularly important in microarray approaches because in these approaches the number of expressed sequences to be tested for, is limited by the number of sequences that an array can maximally hold. With means and methods of the invention it is possible to limit the number of sequences to be tested in microarray approaches.

Yet another use of a system or library is the discovery of drug targets. Regulatory elements, be they "higher order" elements or not, function because of the protein (complexes) that can bind to them. A system of the invention can be used to determine whether targeting of drugs to interfere with the binding or function of a particular protein (complex) holds promise for the alteration of expression of a particular gene.

It is also possible to provide a DNA construct with a DNA sequence of the invention, or to modify such a DNA sequence. In certain embodiments, a DNA construct is provided comprising a promoter operably linked with a nucleic acid of interest. Preferably, the amount of activity of a quality of the DNA sequence with a gene transcription modulating quality, is dependent on the orientation of the DNA sequence in the construct, compared to the promoter. The gene transcription modulating quality may be dependent on the presence of a signal. The signal may comprise a DNA binding protein or a human immuno-deficiency virus TAT protein.

One of the uses of a DNA sequence comprising a gene transcription modulating quality is of course the regulation of transcription of a gene of interest. Transcription of a gene of interest can be altered by altering sequences in the vicinity of the gene such that a DNA sequence with the quality is provided or removed. Specific expression characteristics can be designed by combining (parts of) DNA sequences with a gene transcription modulating quality. For instance, duplication of a sequence with a stable gene transcription quality in an expression vector will lead to improved stability of expression in a target cell or progeny upon introduction of the vector in the target cell. By combining DNA sequences with gene transcription modulating qualities altered gene transcription modulating qualities can be generated either in kind or amount or both.

It is also possible to design DNA sequences with a desired gene transcription modulating quality. DNA binding proteins together with other proteins and DNA sequences determine qualities of the DNA sequence. It is possible to insert one or more other protein binding DNA sequences into a DNA sequence with a quality. By allowing binding of the binding protein(s) it is possible to interfere with, or direct, the quality, thus allowing the generation of DNA sequences with designer qualities. It is also possible to remove protein binding sites from a DNA sequence with a particular gene transcription modulating quality thereby altering the quality of the resulting DNA sequences. The combination of addition and removal is also possible. Particular gene transcription modulating qualities can be selected for by tuning detection methods described in the present invention. It is, for instance, possible to synthesize DNA sequences with inducible gene transcription modulating qualities. There are DNA binding proteins available that only bind to their target sequence in the absence or presence of a signal. Non-limiting examples of such proteins are the TET-repressor and the various mutations thereof, the lac-repressor, steroid hormone receptors, the retinoic acid receptor, and derivatives. It is possible for instance to design a DNA sequence with a cell type specific gene transcription modulating quality. The DNA sequence can be made specific for a protein complex that is expressed in a cell type specific fashion.

Expression constructs comprising a DNA sequence comprising a gene transcription modulating quality are suitable for obtaining expression from the construct in cells comprising more than one copy of the expression construct. Also when the expression construct is present in the genome of the cell and, also when the expression cassette is present in more than one copy in the cell. Moreover, they even work when integrated into the same position in more than one copy.

In certain embodiments, of the invention the DNA sequence with a gene transcription modulating quality comprises a so-called STAR (Stabilizing Anti-Repression) sequence. A STAR sequence as used herein refers to a DNA sequence comprising one or more of the mentioned gene transcription modulating qualities.

Several methods are presented herein to determine whether a sequence comprises STAR activity. STAR activity is confirmed if the sequence is capable of performing at least one of the following functions: (i) at least in part inhibiting the effect of sequence comprising a gene transcription repressing element of the invention, (ii) at least in part blocking chromatin-associated repression, (iii) at least in part blocking activity of an enhancer, (iv) conferring upon an operably linked nucleic acid encoding a transcription unit compared to the same nucleic acid alone. (iv-a) a higher predictability of transcription, (iv-b) a higher transcription, and/or (iv-c) a higher stability of transcription over time.

The large number of sequences comprising STAR activity identified in the present invention opens up a wide variety of possibilities to generate and identify sequences comprising the same activity in kind not necessarily in amount. For instance, it is well within the reach of a skilled person to alter the sequences identified in the present invention and test the altered sequences for STAR activity. Such altered sequences are therefore also part of the present invention. Alteration can include deletion, insertion and mutation of one or more bases in the sequences.

Sequences comprising STAR activity were identified in stretches of 400 bases. However, it is expected that not all of these 400 bases are required to retain STAR activity. Methods to delimit the sequences that confer a certain property to a fragment of between 400 and 5000 bases are well known. The minimal sequence length of a fragment comprising STAR activity is estimated to be about 50 bases.

STAR activity is a feature shared by the sequences listed in SEQ ID NOS: 1-65.

In another aspect, also provided is an isolated and/or recombinant nucleic acid sequence comprising a STAR sequence obtainable by a method of the invention.

As mentioned above, a STAR sequence can exert its activity in a directional way, i.e. more to one side of the fragment containing it than to the other. Moreover, STAR activity can be amplified in amount by multiplying the number of STAR elements. The latter suggests that a STAR element may comprise one or more elements comprising STAR activity.

The term quality in relation to a sequence refers to an activity of the sequence. The term STAR, STAR sequence or STAR element, as used herein, refers to a DNA sequence comprising one or more of the mentioned gene transcription modulating qualities. The term "DNA sequence" as used herein does, unless otherwise specified, not refer to a listing of specific ordering of bases but rather to a physical piece of DNA. A transcription quality with reference to a DNA sequence refers to an effect that the DNA sequence has on transcription of a gene of interest. "Quality" as used herein refers to detectable properties or attributes of a nucleic acid or protein in a transcription system.

The invention is further described with the aid of the following illustrative EXAMPLES.

EXAMPLES

Example 1

Methods to Isolate STAR Elements

Materials and methods: Plasmids and strains. The selection vector for STAR elements, pSelect-SV40-zeo ("pSelect", FIG. 1) is constructed as follows: the pREP4 vector (Invitrogen V004-50) is used as the plasmid backbone. It provides the Epstein Barr oriP origin of replication and EBNA-1 nuclear antigen for high-copy episomal replication in primate cell lines; the hygromycin resistance gene with the thymidine kinase promoter and polyadenylation site, for selection in mammalian cells; and the ampicillin resistance gene and colE1 origin of replication for maintenance in *Escherichia coli*. The vector contains four consecutive LexA operator sites between XbaI and NheI restriction sites (Bunker and Kingston, 1994). Embedded between the LexA operators and the NheI site is a polylinker consisting of the following restriction sites: HindIII-AscI-BamHI-AscI-HindIII. Between the NheI site and a SalI site is the Zeocin resistance gene with the SV40 promoter and polyadenylation site, derived from pSV40/Zeo (Invitrogen V502-20); this is the selectable marker for the STAR screen.

Figure 2:
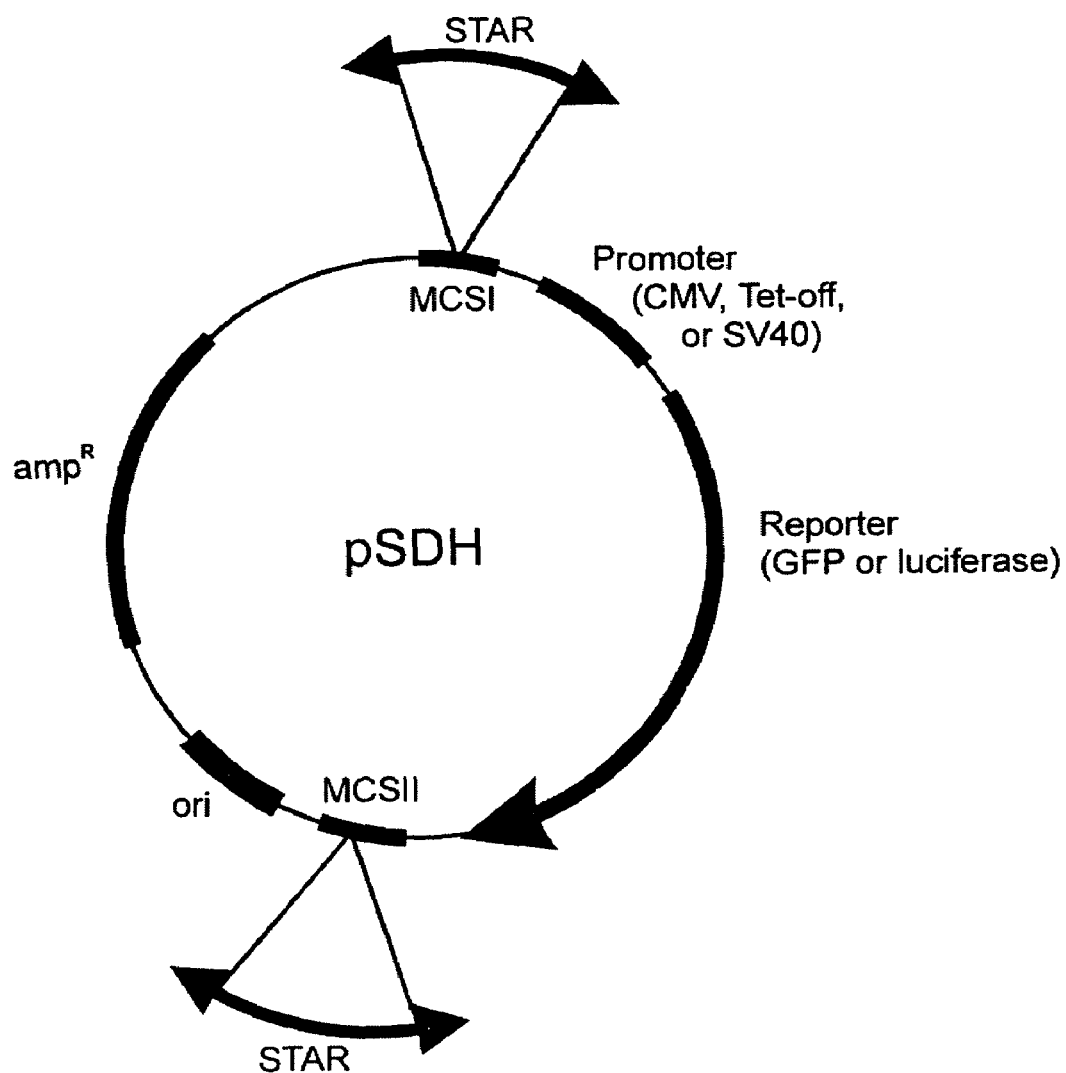
FIG. 2. The pSDH family of plasmids for testing STAR elements. Two multiple cloning sites (MCSI and MCSII) flank a reporter gene (GFP or luciferase) whose expression is driven by an upstream promoter (CMV, Tet-off, or SV40). STAR elements to be tested are inserted at MCSI and MCSII. These contain unique restriction sites (MCSI: XhoI, NotI, EcoRI, and SalI; MCSII: HindIII, EcoRV, BglII, and NheI). The plasmid replicates after integrating at random in the genome of mammalian cells.

The pSDH vector (FIG. 2) is constructed as follows: The luciferase reporter gene from pGL3-Control (Promega E1741) is amplified by PCR and inserted into SacII/BamHI-digested pUHD10-3 (Gossen and Bujard, 1992). This places luciferase under control of the Tet-Off promoter, and upstream of the SV40 polyadenylation signal. Multiple cloning sites are introduced by PCR, upstream of the Tet-Off promoter (MCSI, XhoI-NotI-EcoRI-SalI) and downstream of the polyadenylation signal (MCSII, NheI-BglII-EcoRV-HindIII).

Gene libraries are constructed by Sau3AI digestion of human genomic DNA, either purified from placenta (Clontech 6550-1) or carried in bacterial/P1 (BAC/PAC) artificial chromosomes. The BAC/PAC clones contain genomic DNA from the 1q12 cytogenetic region (clones RP1154H19 and RP3328E19) or from the HOX cluster of homeotic genes (clones RP1167F23, RP1170019, and RP11387A1). The DNAs are size-fractionated, and the 0.5-2 kb size fraction is ligated into BamHI-digested pSelect vector, by standard techniques (Sambrook et al., 1989).

The construction of the host strains has been described (van der Vlag et al., 2000). Briefly, they are based on the U-2 OS human osteosarcoma cell line AMERICAN TYPE CULTURE COLLECTION® HTB-96). U-2 OS is stably transfected with the pTet-Off plasmid (Clontech K1620-A), encoding a protein chimera consisting of the Tet-repressor DNA binding domain and the VP16 transactivation domain. The cell line is subsequently stably transfected with fusion protein genes containing the LexA DNA binding domain, and the coding regions of either HP1 or HPC2 (two *Drosophila* Polycomb group proteins that repress gene expression when tethered to DNA). The LexA-repressor genes are under control of the Tet-Off transcriptional regulatory system (Gossen and Bujard, 1992).

Library screening and STAR element characterization. The gene libraries in pSelect are transfected into the U-2 OS/Tet-Off/LexA-repressor cell line by calcium phosphate precipitation (Graham and van der Eb, 1973; Wigler et al., 1978) as recommended by the supplier of the transfection reagent (Life Technologies). Transfected cells are cultured under hygromycin selection (25 µg/ml) and tetracycline repression (doxycycline, 10 ng/ml) for 1 week (50% confluence). Then the doxycycline concentration is reduced to 0.1 ng/ml to induce the LexA-repressor genes, and after 2 days Zeocin is added to 250 µg/ml. The cells are cultured for a further 4-5 weeks, until the control cultures (transfected with empty pSelect) are killed by the Zeocin.

Zeocin-resistant colonies from the library transfection are propagated, and plasmid DNA is isolated and rescued into *E. coli* by standard techniques (Sambrook et al., 1989). The candidate STAR elements in the rescued DNA are analyzed by restriction endonuclease mapping (Sambrook et al., 1989), DNA sequence analysis (Sanger et al., 1977), and for STAR activity (Zeocin resistance) after re-transfection to U-2 OS/Tet-Off/LexA-repressor and lowering the doxycycline concentration.

Candidate STAR elements that have DNA sequence corresponding to known sequence in the human genome are identified by BLAST searches (Altschul et al., 1990) of the human genome database (www.ncbi.nlm.nih.gov/genome/seq/HsBlast.html 20 Jun. 2001). The chromosomal locations of the elements are recorded, along with the proportion of repetitive DNA and the identity of adjacent genes.

Those candidates that show STAR activity upon re-transfection are characterized further by subcloning the STAR fragment into the pSDH plasmid and stable integration in U-2 OS chromosomal DNA. pSDH plasmids are co-transfected into U-2 OS cells with pBABE-puro (Morgenstern and Land, 1990), and selected for puromycin resistance. Per STAR element, populations of approximately 30 individual clones are isolated and cultured. The clones are periodically assayed for luciferase activity according to the manufacturer's instructions (Roche 1669893).

Results: STAR element functional characterization. The screens of human genomic DNA and of the HOX and 1q12 loci yielded 17 bona fide STAR elements. The criteria are that (1) the elements displayed STAR activity upon re-transfection of the pSelect-based clones into the host U-2 OS human osteosarcoma cell line (indicating that the anti-repressor activity expressed in the initial screen is plasmid-specific and not due to artifactual changes in the host cells); (2) the elements contain DNA sequence that matches sequence in the human genome sequence database (indicating that the clone does not contain contaminating DNA sequence, from e.g., bacterial or vector sources).

The STAR elements are sub-cloned into the pSDH plasmid and integrated into the host cell genome. Expression of the reporter genes is assayed in populations of stable transfectants to demonstrate the ability of the STAR elements to protect reporter genes from silencing after integration at random into the genome. This provides information (1) on the proportion of clones which display high expression, and (2) on the degree of over-expression elicited by the STAR elements.

Figure 3:
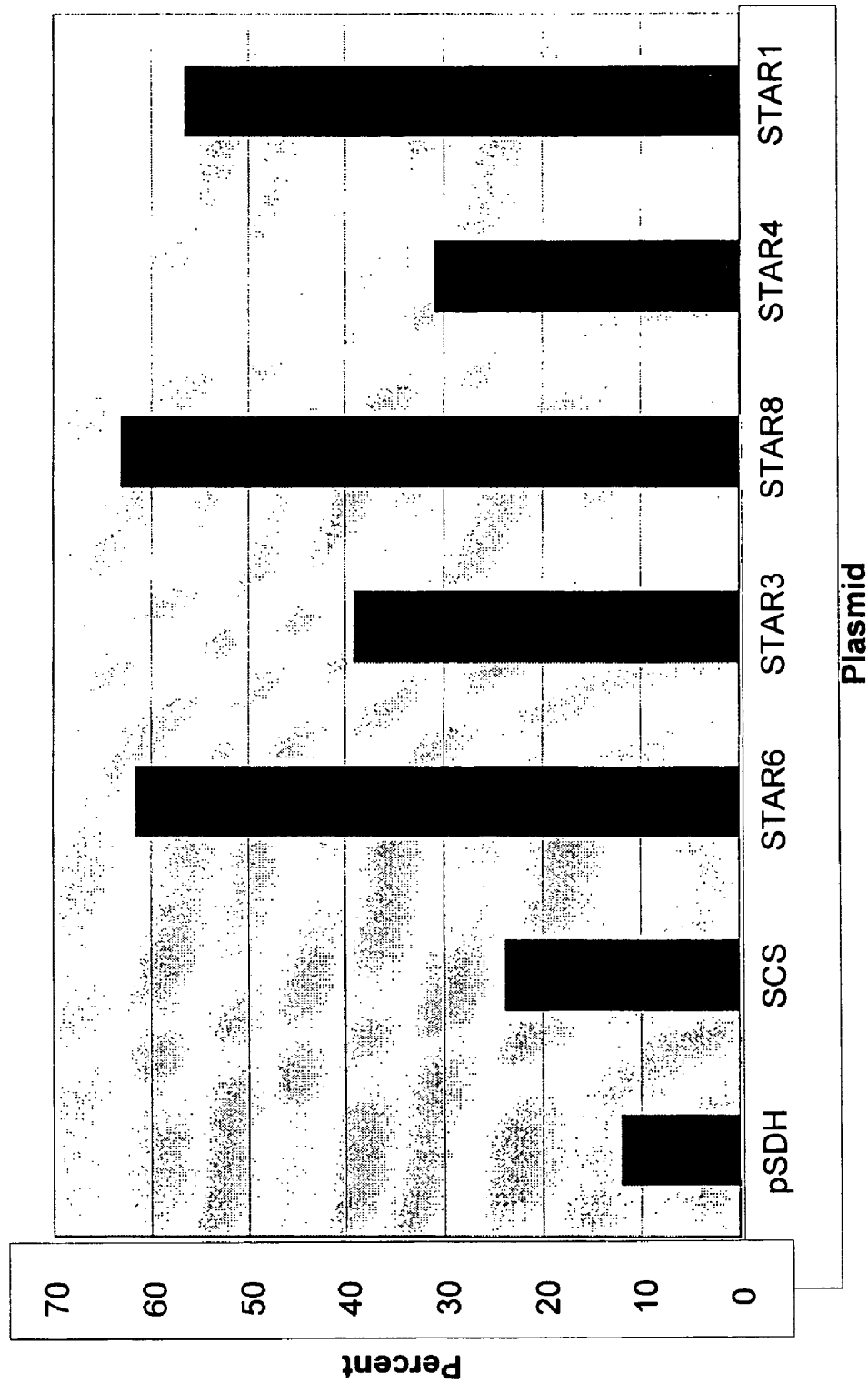
FIG. 3. Proportion of clones over-expressing luciferase. U-2 OS human osteosarcoma cells were stably transfected with pSDH plasmids (containing the luciferase reporter gene under control of the tet-off promoter), and individual transfected clones were isolated and cultivated. Luciferase expression was measured enzymatically. The average luciferase expression by clones containing the STARless pSDH ("reference level") was determined. Clones from the sets for all plasmids were scored as "over-expressing" if their luciferase activity was more than 2-fold higher than the reference level. The percentage of over-expressing clones in each plasmid set is plotted.
Figure 4:
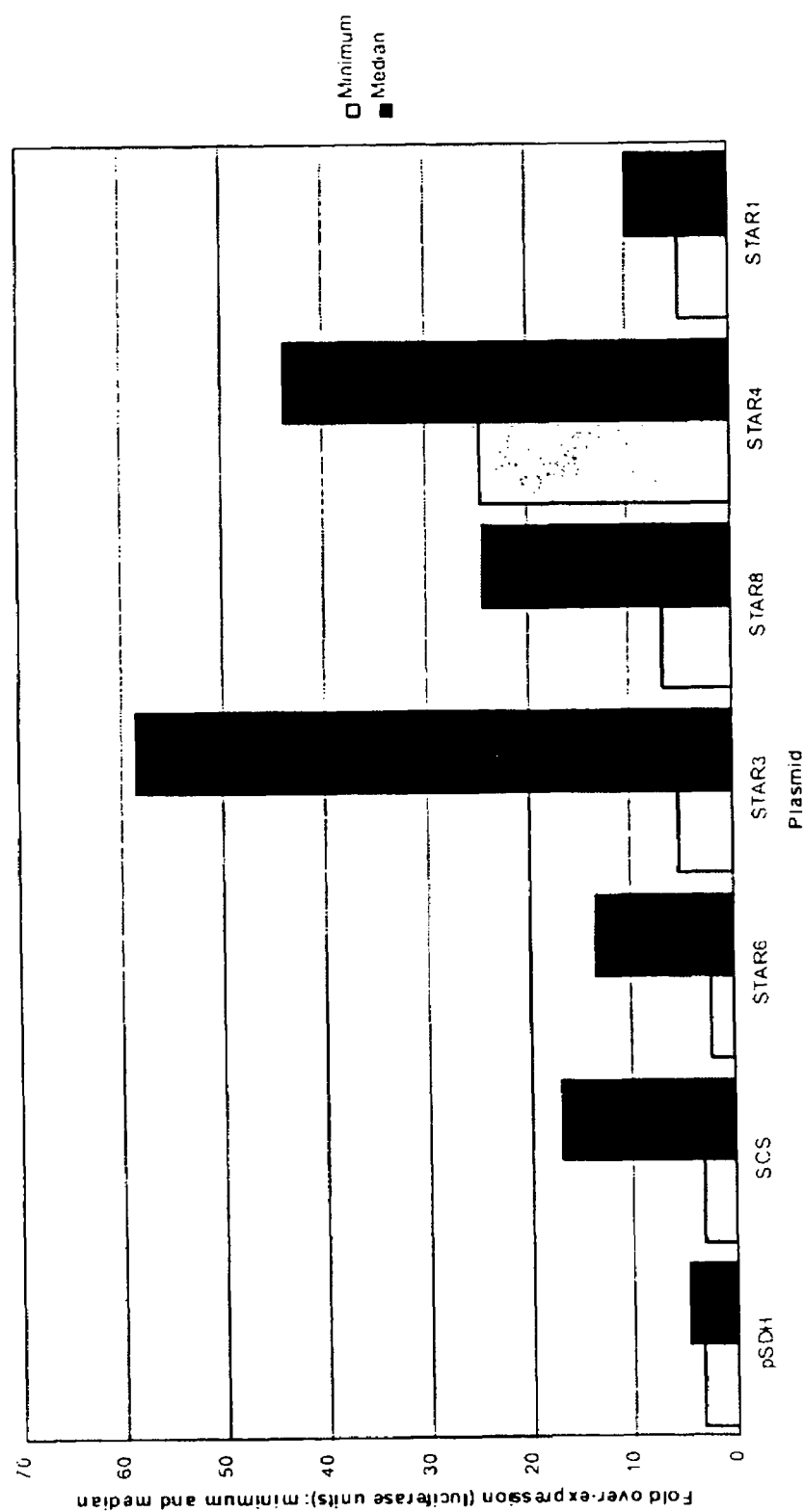
FIG. 4. Fold over-expression by over-expressing clones. The range of over-expression in STAR-containing pSDH plasmids integrated into genomic DNA was determined by dividing the luciferase activities of each clone by the reference level. For those displaying significant expression (more than 2-fold above the reference level), the actual fold increases were noted; the minimum and median values of these data are plotted for each plasmid.
Figure 5:
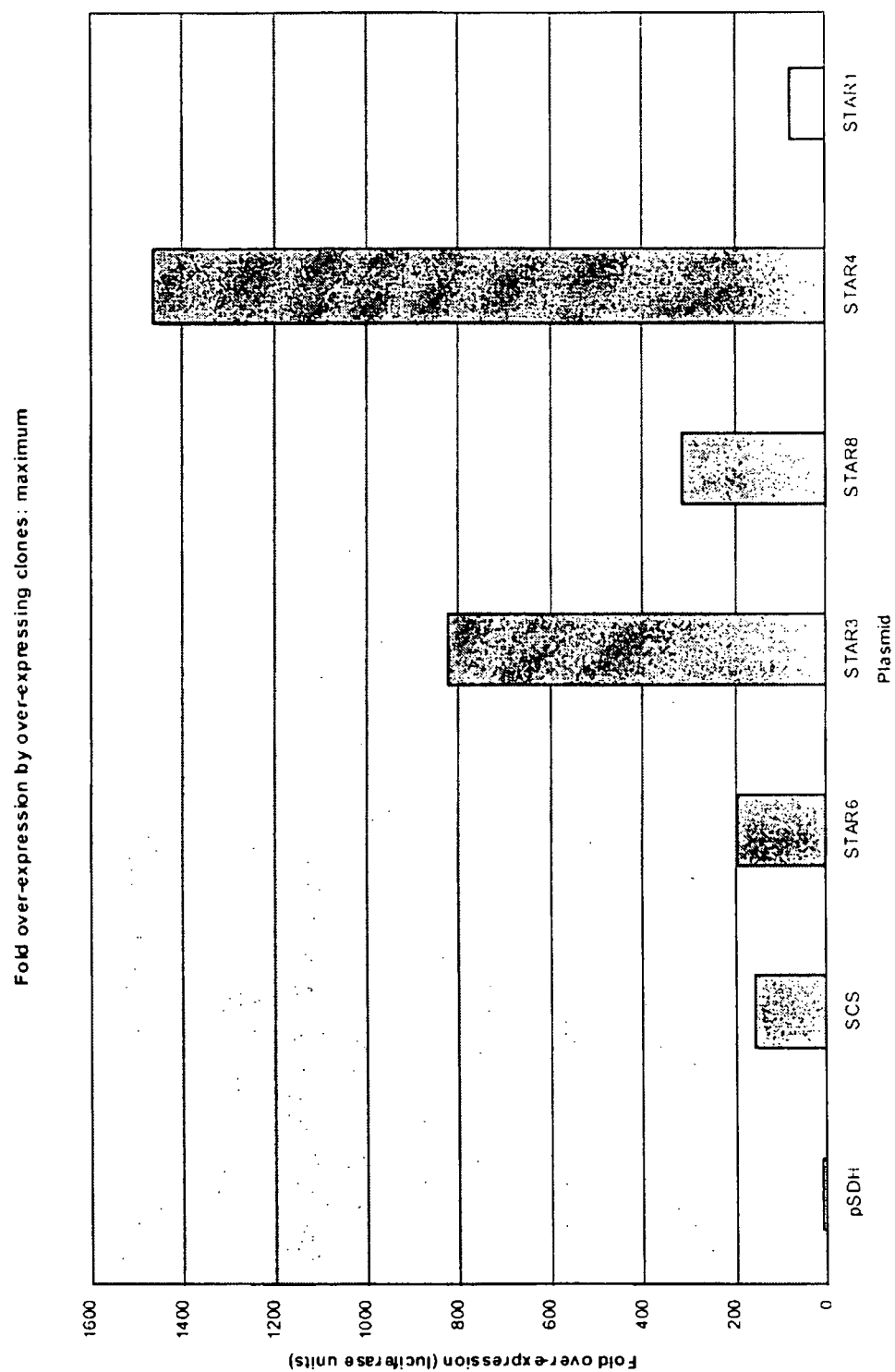
FIG. 5. Fold over-expression by over-expressing clones. The range of over-expression in STAR-containing pSDH plasmids integrated into genomic DNA was determined by dividing the luciferase activities of each clone by the reference level. For those displaying significant expression (more than 2-fold above the reference level), the actual fold increases were noted; the maximum values of these data are plotted for each plasmid.

Expression of the luciferase reporter gene by a clone is considered significant if it is two-fold above the average level for the plasmids containing no STAR elements (the reference level). For all plasmids a distribution in expression level is observed among the clones: from no expression to expression significantly above the reference level, and from few overexpressers to many over-expressers. Superior STAR activity is manifested by plasmids that result in many over-expressing clones, including some highly over-expressing clones. Results from a representative experiment are shown in Table 1, and in FIGS. 3-5.

The results indicate that the human STAR elements which are tested yield a much higher proportion of over-expressing clones than the unprotected reporter gene, or the reporter gene protected by the *Drosophila* SCS element (Kellum and Schedl, 1992). Furthermore, the degree of over-expression by these plasmids is much greater from the STAR-protected reporter gene than the unprotected or SCS-protected reporter.

STAR element sequence and genomic position data. Table 2 lists the chromosomal locations of each of the 17 STAR elements, as well as the identity of nearby genes and the repetitive DNA content of the elements. The STAR elements are distributed over a number of chromosomes. They are diverse in their actual DNA sequence and repetitive DNA content, and display various degrees of association with neighboring genes.

Example 2

Expression Characteristics of the Transgene that are Due to the STAR

Background: site-specific recombination is used to precisely remove heterologous DNAs from their chromosomal locations. This is routinely carried out by one of two systems: the cre recombinase and loxP target of bacteriophage P1 (Feng et al., 1999), or the FLP recombinase and FRT (FLP recombinase target) of yeast (Wigley et al., 1994). In these systems, a DNA region (usually containing a reporter gene and/or a selectable marker) is flanked in the chromosome by the loxP or FRT target. The activity of the recombinase then catalyzes the precise excision of the DNA region from the chromosome. The recombinase resolves its two recognition sequences to a single site, deleting the sequence between them. Thus, a span of DNA must be flanked by target sites to be subsequently deleted in vivo upon introduction or activation of recombinase (Schwenk et al., 1995; Dymecki, 1996). The Cre and Flp recombinases catalyze recombination between two 13-base-pair inverted repeats, separated by a spacer with a minimum of 6 (loxP) or 8 (FRT) base pairs (Senecoff et al., 1985). The loxP sequence is ATAACTTCGTATA (SEQ ID NO: 120) and the FRT sequence is GAAGTTCCTATAC (SEQ ID NO:121).

Protocol: Using conventional DNA cloning (Sambrook et al., 1989), a reporter gene (encoding a reporter protein, for example green fluorescent protein (GFP) (Bierhuizen et al., 1997) or luciferase (Himes and Shannon, 2000) is constructed that is flanked in a plasmid by a pair of STAR elements. In each case, the elements are themselves flanked by recombinase target sites. One element is flanked by a pair of loxP sites, and the other is flanked by a pair of FRT sites (FIG. 1). Upon transfection the plasmid integrates into the host chromosome in a small percentage of cells, and the integrants are selected by antibiotic resistance.

Using conventional techniques, ("SUPERFECT® Transfection Reagent Handbook," Qiagen, November, 1997) these plasmids are transfected into the U-2 OS human osteosarcoma cell line, and selected for hygromycin resistance. Hygromycin-resistant isolates have the plasmid stably integrated in the genome of the cell line. Individual isolates are propagated in cell culture medium, and the expression of the transgenic reporter gene is assayed, for example by flow cytometry (Stull et al., 2000).

Then using conventional techniques (transfection, or hormone stimulation), the stable isolates from above are treated so as to introduce or activate recombinase activity. This is done sequentially, such that for example the cre recombinase activity catalyzes excision of STAR1, and subsequently FLP recombinase activity catalyzes excision of STAR2. The level of expression of the reporter gene in these cells is assayed and the value compared with the reference value of the parental, STAR-containing isolate.

Example 3

Sequence Analysis of STARs; Determination of Minimal Essential Sequence for Element Function; Sequence Conservation Among Elements; and Properties of Tandem and Multiple Elements Background: DNA fragments containing STAR elements are isolated by genetic selection using the pSelect (FIG. 1) plasmid. This section describes the approach to characterize the DNA sequences within those fragments that have STAR activity.

Protocols: DNA sequence: Oligonucleotides are designed based on the sequence of the pSelect plasmid for sequencing the DNA fragments. The fragments are sequenced using the dideoxy chain termination technique (Sanger et al., 1977). DNA sequences are then localized to chromosome position using the public human genome sequence database (www.ncbi.nlm.nih.gov:80/cgi-bin/Entrez/hum_srch?chr=hum_chr.inf&query). Genes and gene density in the vicinity of the fragment sequence are recorded from the genome sequence annotation. Transcriptional activity of those genes is determined from public databases of DNA microarray (arrays.rockefeller.edu/xenopus/links.html) and SAGE (Serial Analysis of Gene Expression; bioinfo.amc.uva.nl/HTM-bin/index.cgi) data.

Once positional information on STAR sequences is compiled, the data are analyzed in terms of underlying consensus sequences. Consensus sequences or trends (understood by this are local areas rich in particular nucleotide combinations, e.g., rich in C and G bases) are detected using similarity search algorithms such as ClustalW (Higgins et al., 1996) and blosum similarity scoring (Altschul and Gish, 1996). Any underlying consensuses or trends found are then used to identify other potential STARs on a genome scale by performing BLAST searches (Altschul et al., 1990).

Previous research has identified transcriptional regulatory proteins that bind to known insulators and boundary elements (Gaszner et al., 1999; Gerasimova and Corces, 1998). In the described examples, the protein binding sites coincide with DNase I hypersensitive sites which are essential for insulator or boundary function. The hypothesis that STAR elements are also bound by known regulatory proteins is examined by searching the TRANSFAC database of transcription factors (transfac.gbf.de/TRANSFAC/) for sequence motifs that occur in the STAR elements. Sequence motifs that are common among the members of the STAR collections are indicators that the corresponding transcription factor binds to that element.

Minimal essential sequence: Using this sequence knowledge STAR elements are truncated and tested for functionality. This is done using the polymerase chain reaction (PCR) to clone sub-fragments of the STAR-containing fragments into pSelect by standard techniques (Sambrook et al., 1989). The plasmids containing the sub-fragments are transfected into U-2 OS cells and tested for functionality by assaying for antibiotic resistance.

Directionality: The STAR elements are tested for their directionality using the pSelect plasmid. For example, the direction of STAR elements isolated by the pSelect screen is referred to as 5'3' orientation. The orientation of the element is reversed by conventional recombinant DNA techniques (Sambrook et al., 1989). The resulting plasmids are transfected into the U-2 OS cell line and expression of the reporter gene is assayed (Bierhuizen et al., 1997; Himes and Shannon, 2000). The level of expression from the plasmid with the reverse-orientation element is compared to that with the 5'3' orientation. If the reverse-orientation plasmid has similar expression levels, then the STAR element does not display directionality.

Combinations and multiples of elements: To determine whether STAR elements are able to function in mixed pairs, different elements are combined and tested. The analysis is performed in the pSDH plasmid by inserting one STAR element in MCSI and a different STAR in MCSII by recombinant DNA techniques (Sambrook et al., 1989). The resulting plasmids are transfected, and the expression of the reporter gene is assayed (Bierhuizen et al., 1997; Himes and Shannon, 2000); the results are compared with the expression from plasmids containing the same element at MCSI and MCSII; if the expression is similar for the two types of plasmids, then it is concluded that different STAR elements do not interfere with each other.

The strength of single STAR elements is compared with tandem repeats of elements. This is done by concatamerization of the STAR elements of interest with DNA ligase and insertion of the ligation product into the pSDH plasmid by recombinant DNA techniques (Sambrook et al., 1989). The resulting plasmids are transfected into U-2 OS cells, and the expression of the reporter gene is assayed (Bierhuizen et al., 1997; Himes and Shannon, 2000); the results are compared with the expression from plasmids containing single STAR elements.

Example 4

Determination of the Distance over which a STAR Functions

Background: STAR elements are used to optimize expression of single and multiple transgenes. To determine if a single pair of STAR elements can protect large or multiple transgenes from silencing it is necessary to determine the range over which STAR elements act.

Protocol: STAR elements are tested for their functionality over distance using derivative plasmids based on pSelect, as follows. A library of random DNA fragments from 500bp to 10 kb is assembled by standard DNA cloning techniques (Sambrook et al., 1989). Fragments are selected from this library that do not possess STAR activity, by testing in the pSelect plasmid as described above. For STAR elements, these fragments are inserted between the cloning site and the promoter of the reporter gene in the appropriate pSelect plasmid (FIG. 1). This set of plasmids is transfected into the U-2 OS cell line, and expression measured as described above. The strength of reporter gene expression is correlated with the length of the random DNA fragment separating the STAR element from the promoter.

Example 5

Determination of the Maximal Length of STAR Elements

Background: STAR elements are cloned as fragments of DNA recovered using the pSelect plasmid, which is done with genomic DNA fragments less than 2 kb. However, these might be portions of a more extended STAR element. Extended STAR activity is examined by the following experiments.

Protocol: STAR elements cloned in pSelect are mapped to the human genome sequence. In order to determine if they are portions of a more extended STAR element, regions of 4 kb that encompass the clones are amplified by PCR and cloned into the pSelect and/or pSDH plasmid by standard recombinant DNA techniques (Sambrook et al., 1989). The resulting plasmids are transfected into U-2 OS cells and assayed for reporter gene expression as described above; plasmids containing the original 2 kb STAR element are included as a control. Three possible results can be expected: (1) similar expression by the control and extended STAR isolates, demonstrating that the STAR element is confined to the original 2 kb fragment; (2) lower expression by the extended STAR isolates, suggesting that the STAR element is contained within the 2 kb fragment and does not act effectively over a distance or that the extended fragment contains an element with a gene transcription repressing quality; (3) higher expression by the extended STAR isolates, suggesting that the extended region contains a more complete STAR element. In the case of result (3), the exercise is reiterated with a larger PCR fragment of 6 kb.

A STAR element may also be a composite of sites to which various proteins bind. Therefore large DNA fragments with STAR activity could be divisible into smaller fragments with STAR activity (see example 3). Elements that are greater than 2 kb are recognized as STAR elements if they still display STAR activity after truncation to less than 2 kb (including by internal deletion).

Example 6

Methylation and Histone Acetylation States of STAR Elements and of the Adjacent Transgenes Background: The regulatory properties of STAR elements are associated with the local chromatin structure, which is determined by the DNA itself and by DNA-associated proteins. Changes in chromatin structure that are associated with changes in gene expression are often produced by secondary modifications of the macromolecules, especially methylation of DNA or acetylation of histone proteins. Identifying the secondary modifications occurring at STAR elements and at adjacent transgenes provides hallmarks for these elements.

Protocol: DNA methylation: STAR elements are cloned into the pSelect plasmid by standard techniques (Sambrook et al., 1989). U-2 OS cells are stably transfected with these plasmids, and with pSelect lacking a STAR element as a control to determine basal DNA methylation at the reporter gene. Cells are harvested and the chromatin purified by standard procedures (Thomas, 1998). The DNA is digested with the HpaII and MspI restriction endonucleases in separate reactions (Sambrook et al., 1989). Both of these restriction enzymes are able to cut the non-methylated sequence CCGG. When the external C is methylated, both MspI and HpaII cannot cleave. However, unlike HpaII, MspI can cleave the sequence when the internal C is methylated. The DNA is subjected to Southern blotting and the blot is analyzed by indirect end-labeling (Pazin and Kadonaga, 1998). As a control, the corresponding pSelect plasmid as naked, unmethylated DNA, is also cut with the described enzymes and subjected to Southern blotting. Comparison of the different sizes of the DNA fragments reveals whether the DNA is methylated in vivo or not.

Histone acetylation: The same transfected cell lines used for DNA methylation analysis are used for these experiments. The method described below yields a high resolution map of the histone acetylation pattern on the STAR elements and the reporter gene (Litt et al., 2001). Micrococcal nuclease digests of nuclei are fractionated on sucrose gradients, and purified nucleosome monomers and dimers are enriched for acetylated histones by immunoprecipitation with anti-acetylhistone antibodies. The nucleosome fraction and immunoprecipitates are subjected to analysis, for example by real-time PCR (Jung et al., 2000) using primers and a Taqman probe that anneal to the reporter gene or to the STAR element to yield 0.2 kb products, with a moving window of 0.1 kb. The rate of increase of the Taqman probe fluorescent signal during the PCR (which is proportional to the abundance of the template DNA in the sample) is then measured. The ratio of the abundance of the template DNA in the nucleosome fraction and the immunoprecipitates provides a fine-map of the pattern of histone acetylation for each 0.1 kb on the reporter gene and STAR element (or on the reporter gene in the absence of an element).

Example 7

In vivo Nucleosome Positioning and DNAse I Hypersensitive Sites

Background: Chromatin is comprised of DNA, histones, and non-histone proteins. The histones form a core particle that is wrapped by ~150 bp of DNA to make a nucleosome. Nucleosomes are separated by 50-75 bp of linker DNA. Stably positioned nucleosomes on chromosomal DNA repress gene expression, and factors that exclude nucleosomes or otherwise remodel chromatin can overcome this repression. The positioning of nucleosomes in a chromosomal region is analyzed by micrococcal nuclease (MNase) assay; MNase cuts chromatin preferentially in the linker DNA. Similarly, some areas of DNA are constitutively exposed to non-histone proteins, and these are frequently regulatory regions, i.e. sites where cis-acting regulatory factors bind. Experimentally, these site are hypersensitive to digestion by the enzyme DNase I.

Protocol: To determine the position of nucleosomes on the reporter gene and on the STAR elements, MNase is used (Saluz and Jost, 1993). Nuclei are purified from cultured U-2 OS cells and digested with MNase as described above (histone acetylation). To search for DNase I hypersensitive sites in the STAR elements or the reporter gene, purified nuclei are treated with DNase I at an appropriate concentration (e.g., 100 µg/ml genomic DNA and 20-100 U/ml DNaseI), as described (Wallrath et al., 1998). Naked DNA is digested with DNase I as a control. For both techniques, the reporter gene and STAR elements are fine-mapped using primer extension or indirect end-labeling and Southern blotting, as described (Tanaka et al., 1996; van der Vlag et al., 2000). The MNase assay reveals a ladder of discrete bands on an autoradiogram corresponding to the positions of nucleosomes on the STAR elements or the reporter gene. DNase I hypersensitive sites are manifested as discrete bands in the resulting autoradiogram that are absent or less prominent in the naked DNA control.

Example 8

Cell-type, Tissue Dependence, and Promoter Dependence of STAR Elements

Background: It has been reported that some insulators or boundary elements may display tissue specificity (Takada et al., 2000). STAR elements have many features in common with insulators and boundary elements. Both promiscuous and tissue-specific STAR elements have biotechnological value in transgenic applications. The assay described below is performed to assess cell-type dependence. Cell and tissue specificity of the elements are examined further by examining the expression of genes in the vicinity of the elements in the human genome, using public databases of DNA microarray (arrays.rockefeller.edu/xenopus/links.html) and SAGE (Serial Analysis of Gene Expression; bioinfo.amc.uva.nl/HTM-bin/index.cgi) data.

Protocol: STAR elements are tested in the pSDH plasmid. Three cell lines are transfected using standard protocols: the human U-2 OS osteosarcoma cell line (Heldin et al., 1986), the Vero cell line from African green monkey kidney (Simizu et al., 1967), and the CHO cell line from Chinese hamster ovary (Kao and Puck, 1968). Elements able to function in all three cell types are categorized as promiscuous. Those only displaying activity in one or two of the cell-lines are categorized as restricted in their cell-type functionality.

Promoter specificity: STAR elements are currently selected and tested in the context of function with two promoters, the entire cytomegalovirus (CMV) promoter or the Tetracycline Response Element and minimal CMV promoter (in combination with the tTA transcriptional activator). To assess promoter specificity, STAR function is tested with other commonly used viral promoters, namely the simian virus type 40 (SV40) early and late promoters, the adenoviral E1A and major late promoters, and the Rous sarcoma virus (RSV) long terminal repeat (Doll et al., 1996; Smith et al., 2000; Weaver and Kadan, 2000; Xu et al., 1995). Each of these promoters is cloned separately into the pSelect plasmid by standard techniques (Sambrook et al., 1989) along with STAR elements. The resulting plasmids are transfected into the U-2 OS cell line and assayed for reporter gene expression, as described above. The ability of STAR elements to protect against silencing, is determined by comparison with plasmids lacking STAR elements.

Example 9

Methods for Improvement of STAR Elements

Background: Improved STAR elements are developed. Improvements yield increased strength of anti-repressive activity, and elements with inducible and tissue-specific activity. These improvements are made by a combination of techniques.

Protocols: Forced evolution: Error prone PCR (Cherry et al., 1999; Henke and Bomscheuer, 1999) is used to introduce an average of one to two point mutations per element. The mutagenized elements are screened using pSelect plasmids containing reporter-selectable marker fusion proteins by for example fluorescence activated cell sorting and antibiotic resistance (Bennett et al., 1998). Subsequent rounds of error prone PCR and selection are carried out to derive elements with further improvements in activity.

Tandem and heterologous combinations: As described above, tandem and heterologous combinations of elements are tested for activity in comparison with the single elements (example 3).

The relative dominance of STAR elements is tested on a case by case basis. It is used to test the strength of an element; for example, if a new STAR element is dominant to a known, strong element with a gene transcription repressing quality, then the STAR is classified as very strong. The possibility that the dominance relationship between a STAR and an element with a gene transcription repressing quality is cell type-, tissue-, or promoter-specific is also considered (example 8). The dominance test utilizes the pSelect plasmid, with individual elements with a gene transcription repressing quality placed upstream of individual STAR elements by standard recombinant DNA techniques (Sambrook et al., 1989). The plasmids are transfected to U-2 OS cells and reporter gene expression is assayed. STAR dominance is manifested by higher expression than the plasmid with only an element with a gene transcription repressing quality.

Introduction of binding sites for other DNA-binding proteins to STAR elements to add novel characteristics (e.g., inducibility, tissue specificity)

Background: Regulatable STAR elements are created by combining them with binding sites for signal-dependent DNA binding proteins. In one example this would involve juxtaposition of a STAR and a glucocorticoid response element (GRE). In the absence of glucocorticoid stimulation the STAR element would function as described. Upon stimulation, the naturally occurring glucocorticoid receptor binds to the GRE and interferes with STAR function.

Protocol: Using conventional DNA cloning (Sambrook et al., 1989), a GRE is introduced into the pSelect vector adjacent to STAR elements. The plasmid is transfected into U-2 OS cells as described above. Cells are divided into two cultures; one is treated with glucocorticoid (10 µM). Expression of the reporter gene is measured and compared between the two cultures. Differences in expression demonstrate the ability to regulate STAR function by action of a signal-dependent DNA-binding protein.

Promiscuous STAR elements: Testing or enhancing these characteristics involves cultivation in different cell lines, and long term cultivation without antibiotic selection (examples 8 and 10).

Example 10

STAR Elements Obviate the Need for Continuous Selection for Maintenance of the Transgene Background: In transgenesis, reliance on selection markers has two drawbacks: the selection agent is usually expensive and carries a metabolic cost to the cells, and there are regulatory and ethical objections to including selectable markers in transgenic applications, especially if the transgene itself is in the product (e.g., crop plants, gene therapy vectors). STAR elements reduce or eliminate the need to maintain selection after establishing the transgenic isolate. Consequently, the resistance gene can be removed from the transgenic genome by site-specific recombination with diminished loss of transgene expression.

Protocol: Stably transfected U-2 OS cell lines containing chromosomally-integrated STAR elements flanking reporter genes are produced by co-transfection of the pSDH plasmid with a trans-acting antibiotic resistance plasmid as described above. The experiment involves testing the stability of the reporter gene expression level in these cell lines during prolonged (3-6 month) cultivation in the absence of selection. This is tested with STAR elements flanking the luciferase or GFP reporter genes in pSDH plasmids.

The antibiotic resistance gene is removed by constructing an expression plasmid (based on PSDH) in which the antibiotic selection marker is flanked by recombinase target sites. The selectable marker is subsequently excised by recombinase activity, as described above (example 2).

Example 11

Predictability and Yield are Improved by Application of STAR Elements in Expression Systems STAR elements function to block the effect of transcriptional repression influences on transgene expression units. These repression influences can be due to heterochromatin ("position effects", (Boivin & Dura, 1998)) or to adjacent copies of the transgene ("repeat-induced gene silencing", (Garrick et al., 1998)). Two of the benefits of STAR elements for heterologous protein production are increased predictability of finding high-expressing primary recombinant host cells, and increased yield during production cycles. These benefits are illustrated in this example.

Figure 6:
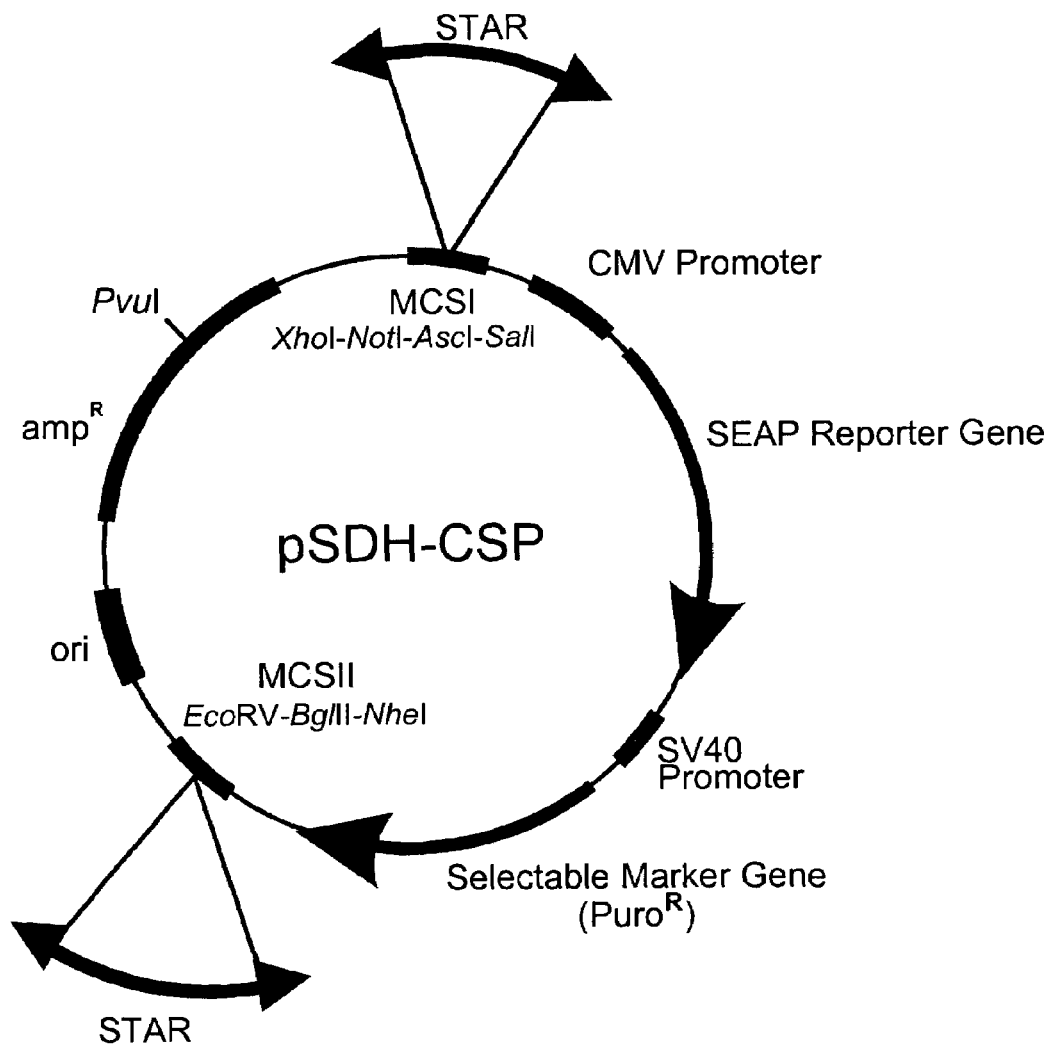
FIG. 6. The pSDH-CSP plasmid used for testing STAR activity. The Secreted Alkaline Phosphatase (SEAP) reporter gene is under control of the CMV promoter, and the puromycin resistance selectable marker (puro) is under control of the SV40 promoter. Flanking these two genes are multiple cloning sites into which STAR elements can be cloned. The plasmid also has an origin of replication (ori) and ampicillin resistance gene (ampR) for propagation in *Escherichia coli*

Materials and Methods: Construction of the pSDH vectors and STAR-containing derivatives: The pSDH-Tet vector was constructed by polymerase chain reaction amplification (PCR) of the luciferase open reading frame from plasmid pREP4-HSF-Luc (van der Vlag et al., 2000) using primers C67 and C68 (all PCR primers and mutagenic oligonucleotides are listed in Table 4), and insertion of the SacII/BamHI fragment into SacII/BamHI-digested pUHD10-3 (Gossen & Bujard, 1992). The luciferase expression unit was re-amplified with primers C65 and C66, and re-inserted into pUHD10-3 in order to flank it with two multiple cloning sites (MCSI and MCSII). An AscI site was then introduced into MCSI by digestion with EcoRI and insertion of a linker (comprised of annealed oligonucleotides D93 and D94). The CMV promoter was amplified from plasmid pCMV-Bsd (Invitrogen K510-01) with primers D90 and D91, and used to replace the Tet-Off promoter in pSDH-Tet by SalI/SacII digestion and ligation to create vector pSDH-CMV. The luciferase open reading frame in this vector was replaced by SEAP (Secreted Alkaline Phosphatase) as follows: vector pSDH-CMV was digested with SacII and BamHI and made blunt; the SEAP open reading frame was isolated from pSEAP-basic (Clontech 6037-1) by EcoRI/SalI digestion, made blunt and ligated into pSDH-CMV to create vector pSDH-CS. The puromycin resistance gene under control of the SV40 promoter was isolated from plasmid pBabe-Puro (Morgenstern & Land, 1990) by PCR, using primers C81 and C82. This was ligated into vector pGL3-control (BamHI site removed) (Promega E1741) digested with NcoI/XbaI, to create pGL3-puro. pGL3-puro was digested with BglII/SalI to isolate the SV40-puro resistance gene, which was made blunt and ligated into NheI digested, blunt-ended pSDH-CS. The resulting vector, pSDH-CSP, is shown in FIG. 6. All cloning steps were carried out following the instructions provided by the manufacturers of the reagents, according to methods known in the art (Sambrook et al., 1989).

STAR elements were inserted into MCSI and MCSII in two steps, by digestion of the STAR element and the pSDH-CSP vector with an appropriate restriction enzyme, followed by ligation. The orientation of STAR elements in recombinant pSDH vectors was determined by restriction mapping. The identity and orientation of the inserts were verified by DNA sequence analysis. Sequencing was performed by the dideoxy method (Sanger et al., 1977) using a Beckman CEQ2000 automated DNA sequencer, according to the manufacturer's instructions. Briefly, DNA was purified from *E. coli* using QIAPREP® Spin Miniprep and Plasmid Midi Kits (QIAGEN 27106 and 12145, respectively). Cycle sequencing was carried out using custom oligonucleotides C85, E25, and E42 (Table 4), in the presence of dye terminators (CEQ Dye Terminator Cycle Sequencing Kit, Beckman 608000).

Transfection and culture of CHO cells with pSDH plasmids: The Chinese Hamster Ovary cell line CHO-K1 (ATCC CCL-61) was cultured in HAMS-F12 medium +10% Fetal Calf Serum containing 2 mM glutamine, 100 U/ml penicillin, and 100 micrograms/ml streptomycin at 37° C./5% C02. Cells were transfected with the pSDH-CSP vector, and its derivatives containing STAR6 or STAR49 in MCSI and MCSII, using SUPERFECT® Transfection Reagent (QIAGEN®) as described by the manufacturer. Briefly, cells were seeded to culture vessels and grown overnight to 70-90% confluence. SUPERFECT® reagent was combined with plasmid DNA (linearized in this example by digestion with PvuI) at a ratio of 6 microliters per microgram (e.g., for a 10 cm Petri dish, 20 micrograms DNA and 120 microliters SUPERFECT®) and added to the cells. After overnight incubation the transfection mixture was replaced with fresh medium, and the transfected cells were incubated further. After overnight cultivation, 5 micrograms/ml puromycin was added. Puromycin selection was complete in 2 weeks, after which time individual puromycin resistant CHO/pSDH-CSP clones were isolated at random and cultured further.

Secreted Alkaline Phosphatase (SEAP) assay: SEAP activity (Berger et al., 1988, Henthom et al., 1988, Kain, 1997, Yang et al., 1997) in the culture medium of CHO/pSDH-CSP clones was determined as described by the manufacturer (Clontech Great EscAPe kit #K2041). Briefly, an aliquot of medium was heat inactivated at 65° C., then combined with assay buffer and CSPD chemiluminescent substrate and incubated at room temperature for 10 minutes. The rate of substrate conversion was then determined in a luminometer (Turner 20/20TD). Cell density was determined by counting trypsinized cells in a COULTER® ACT10 cell counter.

Transfection and culture of U-2 OS cells with pSDH plasmids: The human osteosarcoma U-2 OS cell line (ATCC #HTB-96) was cultured in Dulbecco's Modified Eagle Medium + 10% Fetal Calf Serum containing glutamine, penicillin, and streptomycin (supra) at 37° C./5% CO2. Cells were co-transfected with the pSDH-CMV vector, and its derivatives containing STAR6 or STAR8 in MCSI and MCSII, (along with plasmid pBabe-Puro) using SUPERFECT® Transfection Reagent (supra). Puromycin selection was complete in 2 weeks, after which time individual puromycin resistant U-2 OS/pSDH-CMV clones were isolated at random and cultured further.

Luciferase assay: Luciferase activity (Himes & Shannon, 2000) was assayed in resuspended cells according to the instructions of the assay kit manufacturer (Roche 1669893), using a luminometer (Turner 20/20TD). Total cellular protein concentration was determined by the bicinchoninic acid method according to the manufacturer's instructions (Sigma B-9643), and used to normalize the luciferase data.

Figure 7:
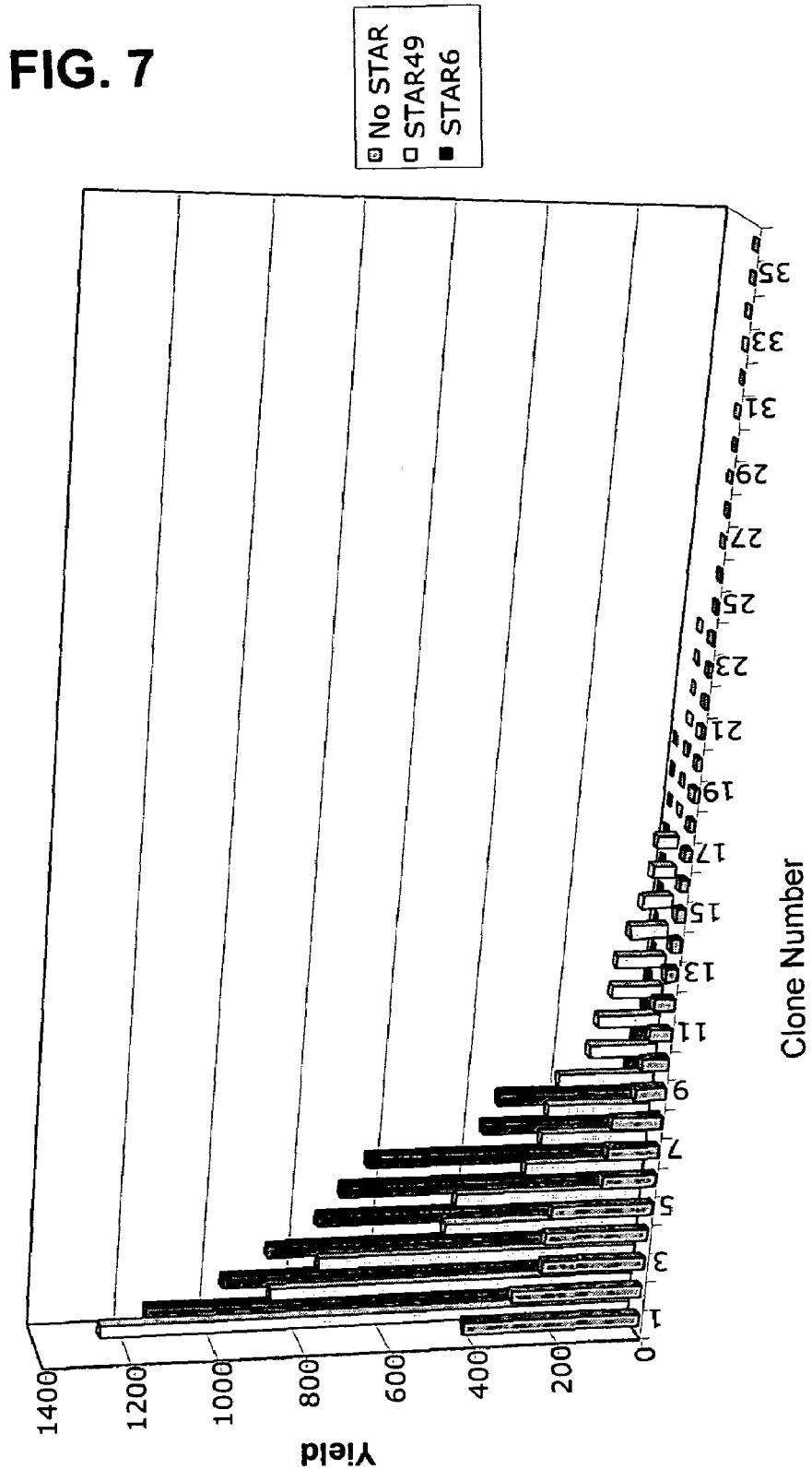
FIG. 7. STAR6 and STAR49 improve predictability and yield of transgene expression. Expression of SEAP from the CMV promoter by CHO cells transfected with pSDH-CSP, pSDH-CSP-STAR6, or pSDH-CSP-STAR49 was determined. The STAR-containing constructs confer greater predictability and elevated yield relative to the pSDH-CSP construct alone.

Results: Recombinant CHO cell clones containing the pSDH-CSP vector, or pSDH-CSP plasmids containing STAR6 or STAR49 (Table 5), were cultured for 3 weeks. The SEAP activity in the culture supernatants was then determined, and is expressed on the basis of cell number (FIG. 7). As can be seen, clones with STAR elements in the expression units were isolated that express 2-3 fold higher SEAP activity than clones whose expression units do not include STAR elements. Furthermore, the number of STAR-containing clones that express SEAP activity at or above the maximal activity of the STAR-less clones is quite high: 25% to 40% of the STAR clone populations exceed the highest SEAP expression of the pSDH-CSP clones.

Recombinant U-2 OS cell clones containing the pSDH-CMV vector, or pSDH-CMV plasmids containing STAR6 or STAR8 (Table 5), were cultured for 3 weeks. The luciferase activity in the host cells was then determined, and is expressed as relative luciferase units (FIG. 8), normalized to total cell protein. The recombinant U-2 OS clones with STAR elements flanking the expression units had higher yields than the STAR-less clones: the highest expression observed from STAR8 clones was 2-3 fold higher than the expression from STAR-less clones. STAR6 clones had maximal expression levels 5 fold higher than the STAR-less clones. The STAR elements conferred greater predictability as well: for both STAR elements, 15 to 20% of the clones displayed luciferase expression at levels comparable to or greater than the STAR-less clone with the highest expression level.

These results demonstrate that, when used with the strong CMV promoter, STAR elements increase the yield of heterologous proteins (luciferase and SEAP). All three of the STAR elements introduced in this example provide elevated yields. The increased predictability conferred by the STAR elements is manifested by the large proportion of the clones with yields equal to or greater than the highest yields displayed by the STAR-less clones.

Example 12

STAR Elements Improve the Stability of Transgene Expression

During cultivation of recombinant host cells, it is common practice to maintain antibiotic selection. This is intended to prevent transcriptional silencing of the transgene, or loss of the transgene from the genome by processes such as recombination. However it is undesirable for production of heterologous proteins, for a number of reasons. First, the antibiotics that are used are quite expensive, and contribute significantly to the unit cost of the product. Second, for biopharmaceutical use, the protein must be demonstrably pure, with no traces of the antibiotic in the product. One advantage of STAR elements for heterologous protein production is that they confer stable expression on transgenes during prolonged cultivation, even in the absence of antibiotic selection; this property is demonstrated in this example.

Materials and Methods: The U-2 OS cell line was transfected with the plasmid pSDH-Tet-STAR6 and cultivated as described in Example 11. Individual puromycin-resistant clones were isolated and cultivated further in the absence of doxycycline. At weekly intervals the cells were transferred to fresh culture vessels at a dilution of 1:20. Luciferase activity was measured at periodic intervals as described in Example 11. After 15 weeks the cultures were divided into two replicates; one replicate continued to receive puromycin, while the other replicate received no antibiotic for the remainder of the experiment (25 weeks total).

Results: Table 6 presents the data on luciferase expression by an expression unit flanked with STAR6 during prolonged growth with or without antibiotic. As can be seen, the expression of the reporter transgene, luciferase, remains stable in the U-2 OS host cells for the duration of the experiment. After the cultures were divided into two treatments (plus antibiotic and without antibiotic) the expression of luciferase was essentially stable in the absence of antibiotic selection. This demonstrates the ability of STAR elements to protect transgenes from silencing or loss during prolonged cultivation. It also demonstrates that this property is independent of antibiotic selection. Therefore production of heterologous proteins is possible without incurring the costs of the antibiotic or of difficult downstream processing.

Example 13

Minimal Essential Sequences of STAR Elements

STAR elements are isolated from the genetic screen described in Example 1. The screen uses libraries constructed with human genomic DNA that was size-fractionated to approximately 0.5-2 kilobases (supra). The STAR elements range from 500 to 2361 base pairs (Table 5). It is likely that, for many of the STAR elements that have been isolated, STAR activity is conferred by a smaller DNA fragment than the initially isolated clone. It is useful to determine these minimum fragment sizes that are essential for STAR activity, for two reasons. First, smaller functional STAR elements would be advantageous in the design of compact expression vectors, since smaller vectors transfect host cells with higher efficiency. Second, determining minimum essential STAR sequences permits the modification of those sequences for enhanced functionality. Two STAR elements have been fine-mapped to determine their minimal essential sequences.

Materials and Methods: STAR10 (1167 base pairs) and STAR27 (1520 base pairs) have been fine-mapped. They have been amplified by PCR to yield sub-fragments of approximately equal length (FIG. 9 legend). For initial testing, these have been cloned into the pSelect vector at the BamHI site, and transfected into U-2 OS/Tet-Off/LexA-HP1 cells as described in Example 1. After selection for hygromycin resistance, LexA-HP1 was induced by lowering the doxycycline concentration. Transfected cells were then incubated with Zeocin to test the ability of the STAR fragments to protect the SV40-Zeo expression unit from repression due to LexA-HP1 binding.

Results: In this experiment STAR10 and STAR 27 confer good protection against gene silencing, as expected (FIG. 9). This is manifested by robust growth in the presence of Zeocin.

Of the 3 STAR10 sub-fragments, 10A (~400 base pairs) confers on transfected cells vigorous growth in the presence of Zeocin, exceeding that of the full-length STAR element. Cells transfected with pSelect constructs containing the other 2 sub-fragments do not grow in the presence of Zeocin. These results identify the ~400 base pair 10A fragment as encompassing the DNA sequence responsible for the anti-repression activity of STAR10.

STAR27 confers moderate growth in Zeocin to transfected cells in this experiment (FIG. 9). One of the sub-fragments of this STAR, 27B (~500 base pairs), permits weak growth of the host cells in Zeocin-containing medium. This suggests that the anti-repression activity of this STAR is partially localized on sub-fragment 27B, but full activity requires sequences from 27A and/or 27C (each ~500 base pairs) as well.

Example 14

STAR Elements Function in Diverse Strains of Cultured Mammalian Cells

The choice of host cell line for heterologous protein expression is a critical parameter for the quality, yield, and unit cost of the protein. Considerations such as post-translational modifications, secretory pathway capacity, and cell line immortality dictate the appropriate cell line for a particular biopharmaceutical production system. For this reason, the advantages provided by STAR elements in terms of yield, predictability, and stability should be obtainable in diverse cell lines. This was tested by comparing the function of STAR6 in the human U-2 OS cell line in which it was originally cloned, and the CHO cell line which is widely applied in biotechnology.

Materials and Methods: The experiments of Example 11 are referred to.

Results: The expression of the SEAP reporter gene in CHO cells is presented in FIG. 7; the expression of the luciferase reporter gene in U-2 OS cells is presented in FIG. 8. By comparison of the results of these two experiments, it is apparent that the STAR6 element is functional in both cell lines: reporter gene expression was more predictable in both of them, and clones of each cell line displayed higher yields, when the reporter gene was shielded from position effects by STAR6. These two cell lines are derived from different species (human and hamster) and different tissue types (bone and ovary), reflecting the broad range of host cells in which this STAR element can be utilized in improving heterologous protein expression.

Example 15

STAR Elements Function in the Context of Various Transcriptional Promoters

Transgene transcription is achieved by placing the transgene open reading frame under control of an exogenous promoter. The choice of promoter is influenced by the nature of the heterologous protein and the production system. In most cases, strong constitutive promoters are preferred because of the high yields they can provide. Some viral promoters have these properties; the promoter/enhancer of the cytomegalovirus immediate early gene ("CMV promoter") is generally regarded as the strongest promoter in common biotechnological use (Boshart et al., 1985, Doll et al., 1996, Foecking & Hofstetter, 1986). The simian virus SV40 promoter is also moderately strong (Boshart et al., 1985, Foecking & Hofstetter, 1986) and is frequently used for ectopic expression in mammalian cell vectors. The Tet-Off promoter is inducible: the promoter is repressed in the presence of tetracycline or related antibiotics (doxycycline is commonly used) in cell-lines which express the tTA plasmid (Clontech K1620-A), and removal of the antibiotic results in transcriptional induction (Deuschle et al., 1995, Gossen & Bujard, 1992, Izumi & Gilbert, 1999, Umana et al., 1999).

Materials and Methods: The construction of the pSDH-Tet and pSDH-CMV vectors is described in Example 11. pSDH-SV40was constructed by PCR amplification of the SV40promoter (primers D41 and D42) from plasmid pSelect-SV40-Zeo (Example 1), followed by digestion of the PCR product with SacII and SalI. The pSDH-CMV vector was digested with SacII and SalI to remove the CMV promoter, and the vector and SV40fragment were ligated together to create pSDH-SV40. STAR6 was cloned into MCSI and MCSII as described in Example 11. The plasmids pSDH-Tet, pSDH-Tet-STAR6, pSDH-Tet-STAR7, pSDH-SV40and pSDH-SV40-STAR 6 were co-transfected with pBabe-Puro into U-2 OS using SUPERFECT® Transfection Reagent as described by the manufacturer. Cell cultivation, puromycin selection, and luciferase assays were carried out as described in Example 11.

Figure 8:
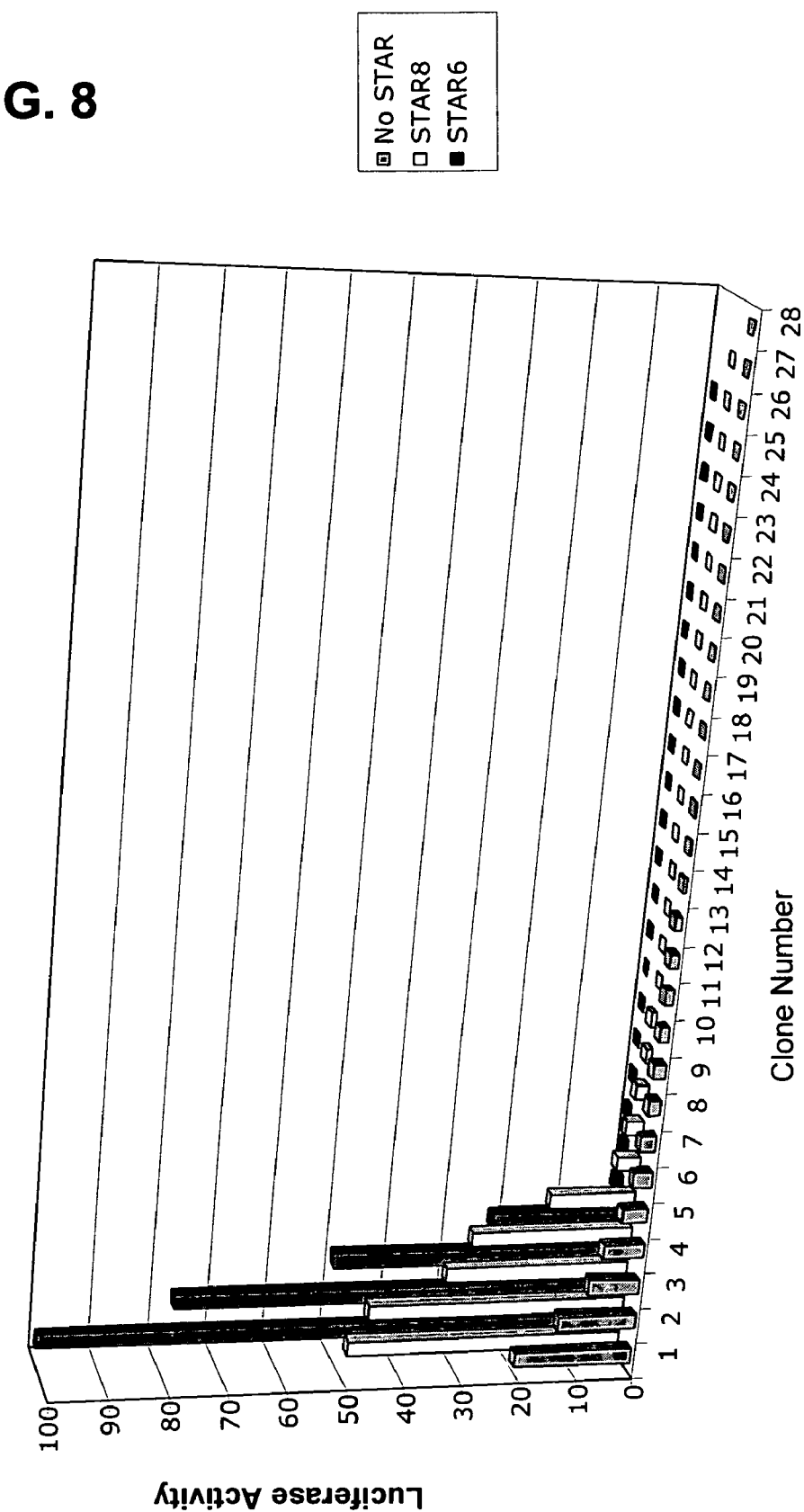
FIG. 8. STAR6 and STAR8 improve predictability and yield of transgene expression. Expression of luciferase from the CMV promoter by U-2 OS cells transfected with pSDH-CMV, pSDH-CMV-STAR6, or pSDH-CMV-STAR8 was determined. The STAR-containing constructs confer greater predictability and elevated yield relative to the pSDH-CMV construct alone.
Figure 10:
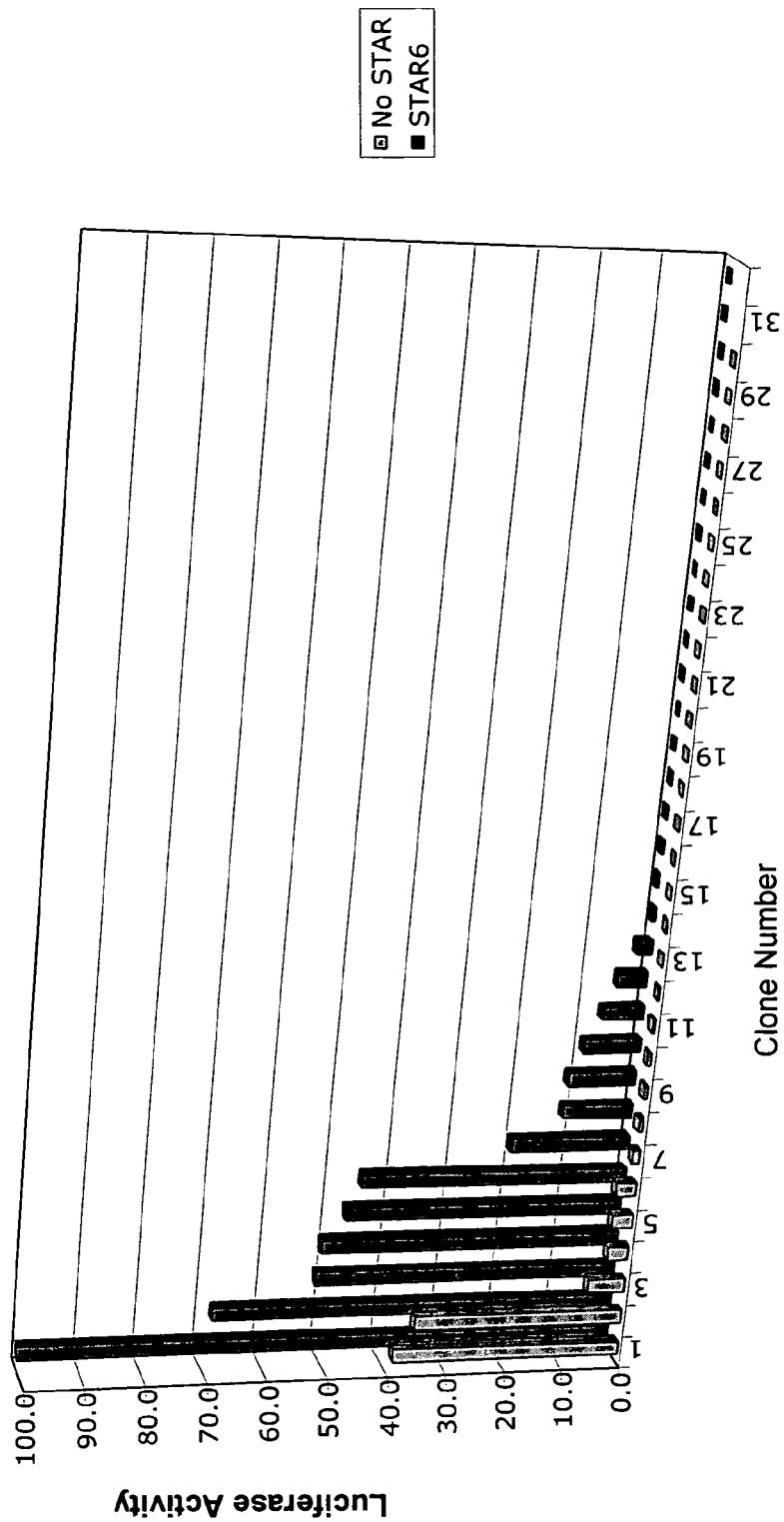
FIG. 10. STAR element function in the context of the SV40 promoter. pSDH-SV40 and pSDH-SV40-STAR6 were transfected into the human osteosarcoma U-2 OS cell line, and expression of luciferase was assayed with or without protection from gene silencing by STAR6 in puromycin-resistant clones.
Figure 11:
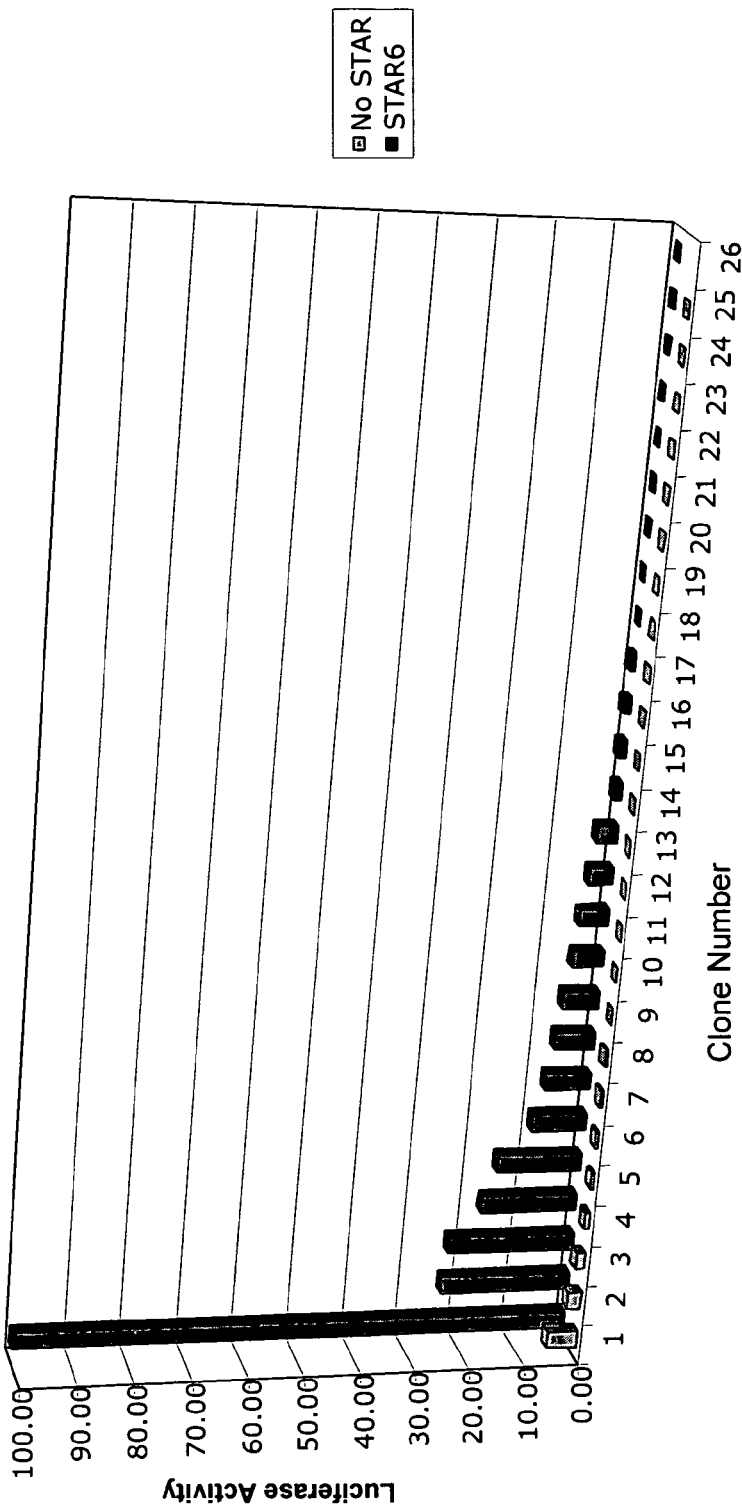
FIG. 11. STAR element function in the context of the Tet-Off promoter. pSDH-Tet and pSDH-Tet-STAR6 were transfected into the human osteosarcoma U-2 OS cell line, and expression of luciferase was assayed with or without protection from gene silencing by STAR6 in puromycin-resistant clones.

Results: FIGS. 8, 10, and 11 compare the expression of the luciferase reporter gene from 3 different promoters: two strong and constitutive viral promoters (CMV and SV40), and the inducible Tet-Off promoter. All three promoters were tested in the context of the STAR6 element in U-2 OS cells. The results demonstrate that the yield and predictability from all 3 promoters are increased by STAR6. As described in Examples 11 and 14, STAR6 is beneficial in the context of the CMV promoter (FIG. 8). Similar improvements are seen in the context of the SV40 promoter (FIG. 10): the yield from the highest-expressing STAR6 clone is 2-3 fold greater than the best pSDH-SV40 clones, and 6 STAR clones (20% of the population) have yields higher than the best STAR-less clones. In the context of the Tet-Off promoter under inducing (low doxycycline) concentrations, STAR6 also improves the yield and predictability of transgene expression (FIG. 11): the highest-expressing STAR6 clone has a 20-fold higher yield than the best pSDH-Tet clone, and 9 STAR6 clones (35% of the population) have yields higher than the best STAR-less clone. It is concluded that this STAR element is versatile in its transgene-protecting properties, since it functions in the context of various biotechnologically useful promoters of transcription.

Example 16

STAR Element Function can be Directional

While short nucleic acid sequences can be symmetrical (e.g., palindromic), longer naturally-occurring sequences are typically asymmetrical. As a result, the information content of nucleic acid sequences is directional, and the sequences themselves can be described with respect to their 5' and 3' ends. The directionality of nucleic acid sequence information affects the arrangement in which recombinant DNA molecules are assembled using standard cloning techniques known in the art (Sambrook et al., 1989). STAR elements are long, asymmetrical DNA sequences, and have a directionality based on the orientation in which they were originally cloned in the pSelect vector. In the examples given above, using two STAR elements in pSDH vectors, this directionality was preserved. This orientation is described as the native or 5'-3' orientation, relative to the Zeocin resistance gene (see FIG. 12). In this example the importance of directionality for STAR function is tested in the pSDH-Tet vector. Since the reporter genes in the pSDH vectors are flanked on both sides by copies of the STAR element of interest, the orientation of each STAR copy must be considered. This example compares the native orientation with the opposite orientation (FIG. 12).

Materials and Methods: The STAR66 element was cloned into pSDH-Tet as described in Example 11. U-2 OS cells were co-transfected with plasmids pSDH-Tet-STAR66-native and pSDH-Tet-STAR66-opposite, and cultivated as described in Example 11. Individual clones were isolated and cultivated; the level of luciferase expression was determined as described (supra).

Figure 13:
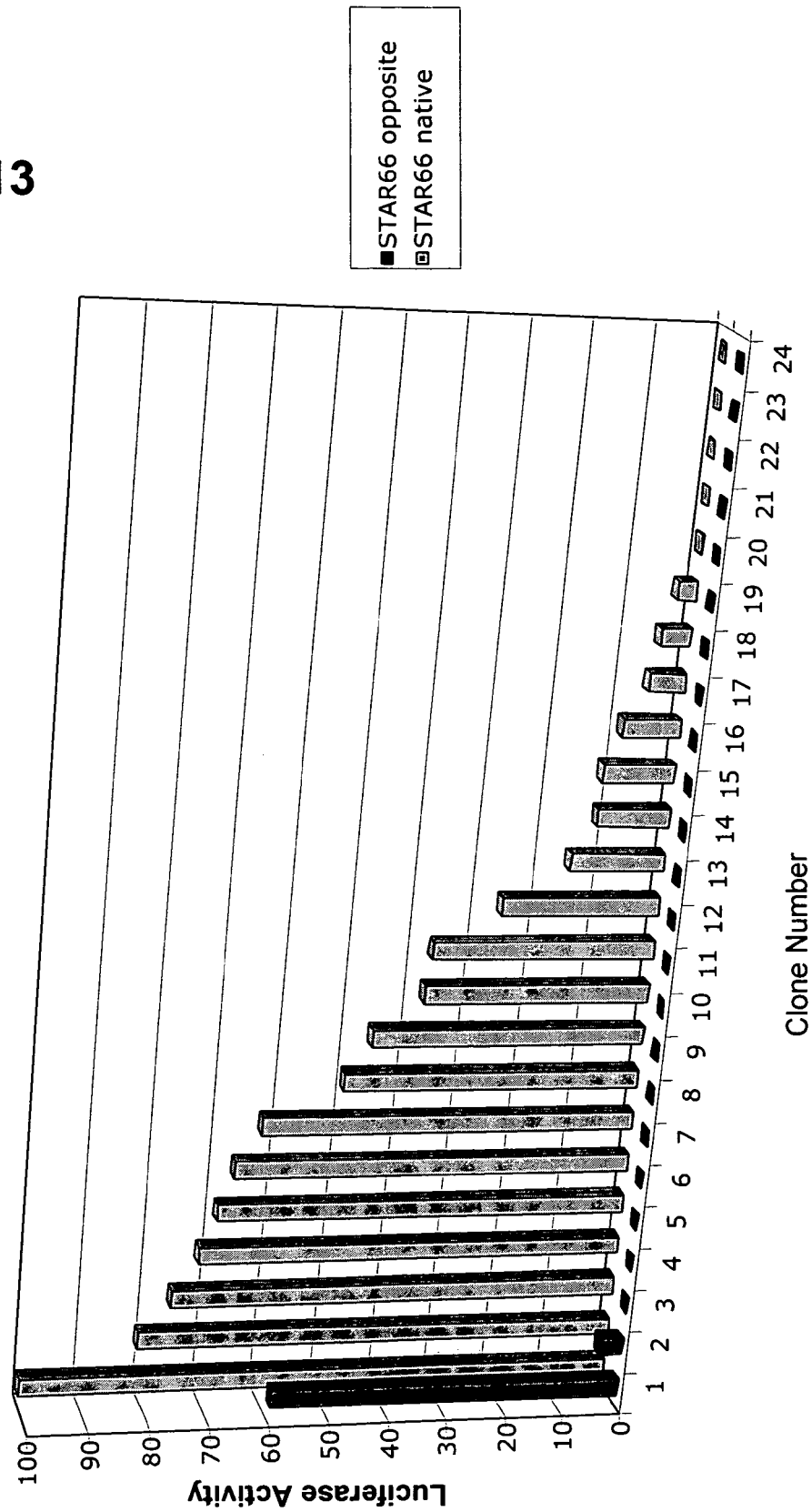
FIG. 13. Directionality of STAR66 function. The STAR66 element was cloned into pSDH-Tet in either the native (STAR66 native) or the opposite orientation (STAR66 opposite), and transfected into U-2 OS cells. Luciferase activity was assayed in puromycin resistant clones.

Results: The results of the comparison of STAR66 activity in the native orientation and the opposite orientation are shown in FIG. 13. When STAR66 is in the opposite orientation, the yield of only one clone is reasonably high (60 luciferase units). In contrast, the yield of the highest-expressing clone when STAR66 is in the native orientation is considerably higher (100 luciferase units), and the predictability is much higher as well: 7 clones of the native-orientation population (30%) express luciferase above the level of the highest-expressing clone from the opposite-orientation population, and 15 of the clones in the native-orientation population (60%) express luciferase above 10 relative luciferase units. Therefore it is demonstrated that STAR66 function is directional.

Example 17

Transgene Expression in the Context of STAR Elements is Copy Number-dependent

Transgene expression units for heterologous protein expression are generally integrated into the genome of the host cell to ensure stable retention during cell division. Integration can result in one or multiple copies of the expression unit being inserted into the genome; multiple copies may or may not be present as tandem arrays. The increased yield demonstrated for transgenes protected by STAR elements (supra) suggests that STAR elements are able to permit the transgene expression units to function independently of influences on transcription associated with the site of integration in the genome (independence from position effects (Boivin & Dura, 1998)). It suggests further that the STAR elements permit each expression unit to function independently of neighboring copies of the expression unit when they are integrated as a tandem array (independence from repeat-induced gene silencing (Garrick et al., 1998)). Copy number-dependence is determined from the relationship between transgene expression levels and copy number, as described in the example below.

Figure 14:
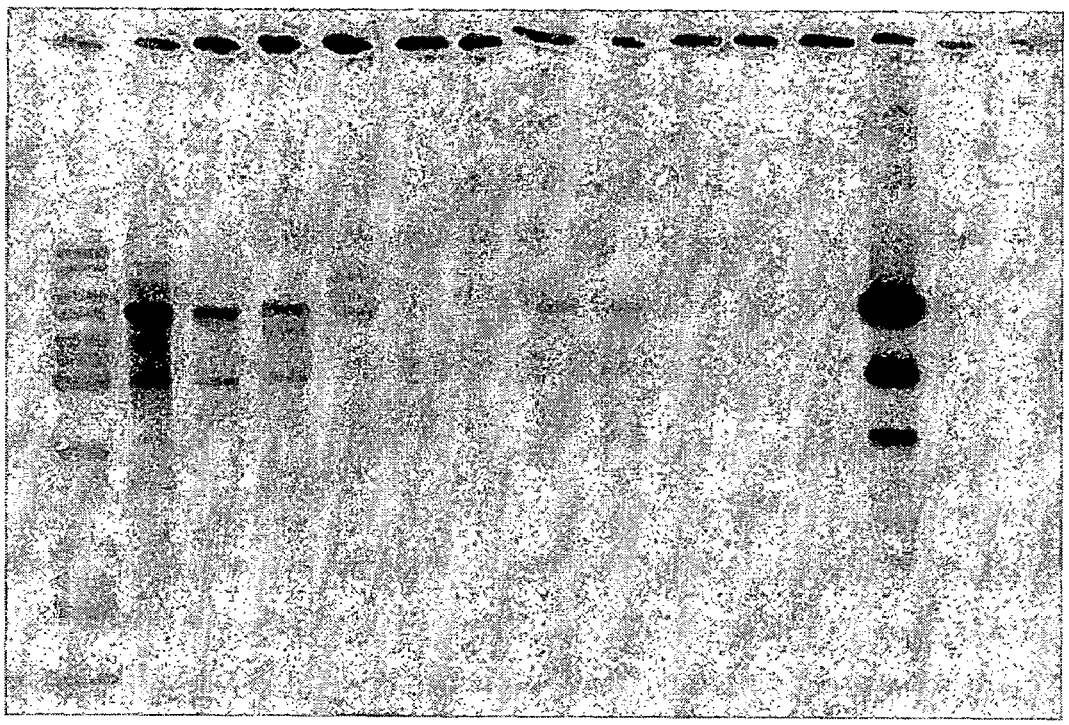
FIG. 14. Copy number-dependence of STAR function. Southern blot of luciferase expression units in pSDH-Tet-STAR10, integrated into U-2 OS genomic DNA. Radioactive luciferase DNA probe was used to detect the amount of transgene DNA in the genome of each clone, which was then quantified with a phosphorimager.

Materials and Methods: U-2 OS cells were co-transfected with pSDH-Tet-STAR10 and cultivated under puromycin selection as described (supra). Eight individual clones were isolated and cultivated further. Then cells were harvested, and one portion was assayed for luciferase activity as described (supra). The remaining cells were lysed and the genomic DNA purified using the DNEASY® Tissue Kit (QIAGEN 69504) as described by the manufacturer. DNA samples were quantitated by UV spectrophotometry. Three micrograms of each genomic DNA sample were digested with PvuII and XhoI overnight as described by the manufacturer (New England Biolabs), and resolved by agarose gel electrophoresis. DNA fragments were transferred to a nylon membrane as described (Sambrook et al., 1989), and hybridized with a radioactively labeled probe to the luciferase gene (isolated from BamHI/SacII-digested pSDH-Tet). The blot was washed as described (Sambrook et al., 1989) and exposed to a phosphonmager screen (Personal F/X, BioRad). The resulting autoradiogram (FIG. 14) was analyzed by densitometry to determine the relative strength of the luciferase DNA bands, which represents the transgene copy number.

Figure 15:
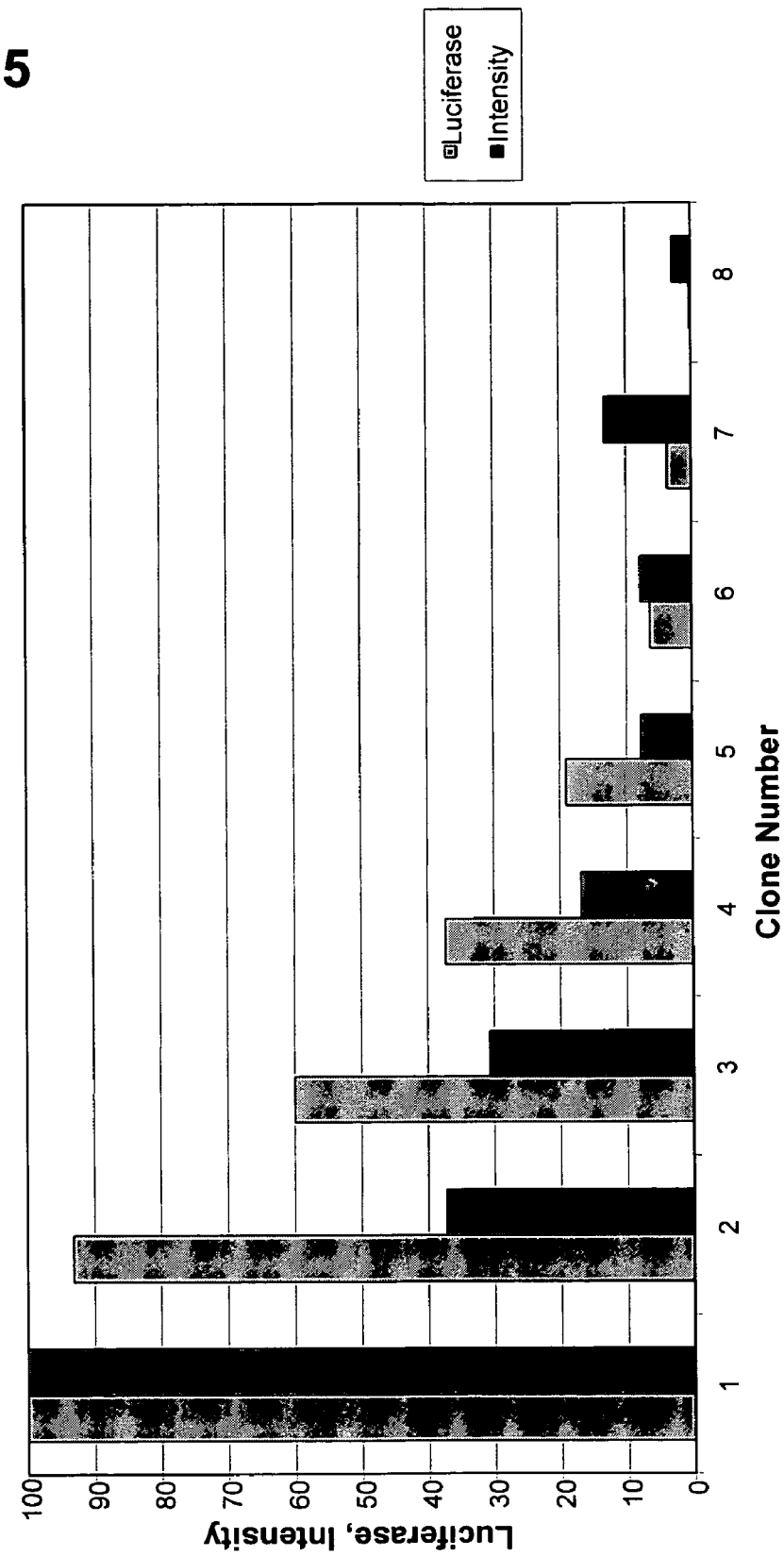
FIG. 15. Copy number-dependence of STAR function. The copy number of pSDH-Tet-STAR10 expression units in each clone was determined by phosphorimagery, and compared with the activity of the luciferase reporter enzyme expressed by each clone.

Results: The enzyme activities and copy numbers (DNA band intensities) of luciferase in the clones from the pSDH-Tet-STAR10 clone population is shown in FIG. 15. The transgene copy number is highly correlated with the level of luciferase expression in these pSDH-Tet-STAR10 clones (r=0.86). This suggests that STAR10 confers copy number-dependence on the transgene expression units, making transgene expression independent of other transgene copies in tandem arrays, and independent of gene-silencing influences at the site of integration.

Example 18

STAR Elements Function as Enhancer Blockers but not Enhancers

Gene promoters are subject to both positive and negative influences on their ability to initiate transcription. An important class of elements that exert positive influences are enhancers. Enhancers are characteristically able to affect promoters even when they are located far away (many kilobase pairs) from the promoter. Negative influences that act by heterochromatin formation (e.g., Polycomb group proteins) have been described above, and these are the target of STAR activity. The biochemical basis for enhancer function and for heterochromatin formation is fundamentally similar, since they both involve binding of proteins to DNA. Therefore it is important to determine whether STAR elements are able to block positive influences as well as negative influences, in other words, to shield transgenes from genomic enhancers in the vicinity of the site of integration. The ability to shield transgenes from enhancer activity ensures stable and predictable performance of transgenes in biotechnological applications. This example examines the performance of STAR elements in an enhancer-blocking assay.

Another feature of STAR activity that is important to their function is the increased yield they confer on transgenes (Example 11). STARs are isolated on the basis of their ability to maintain high levels of Zeocin expression when heterochromatin-forming proteins are bound adjacent to the candidate STAR elements. High expression is predicted to occur because STARs are anticipated to block the spread of heterochromatin into the Zeocin expression unit. However, a second scenario is that the DNA fragments in Zeocin-resistant clones contain enhancers. Enhancers have been demonstrated to have the ability to overcome the repressive effects of Polycomb-group proteins such as those used in the method of the STAR screen (Zink & Paro, 1995). Enhancers isolated by this phenomenon would be considered false positives, since enhancers do not have the properties claimed here for STARs. In order to demonstrate that STAR elements are not enhancers, they have been tested in an enhancer assay.

Figure 16:
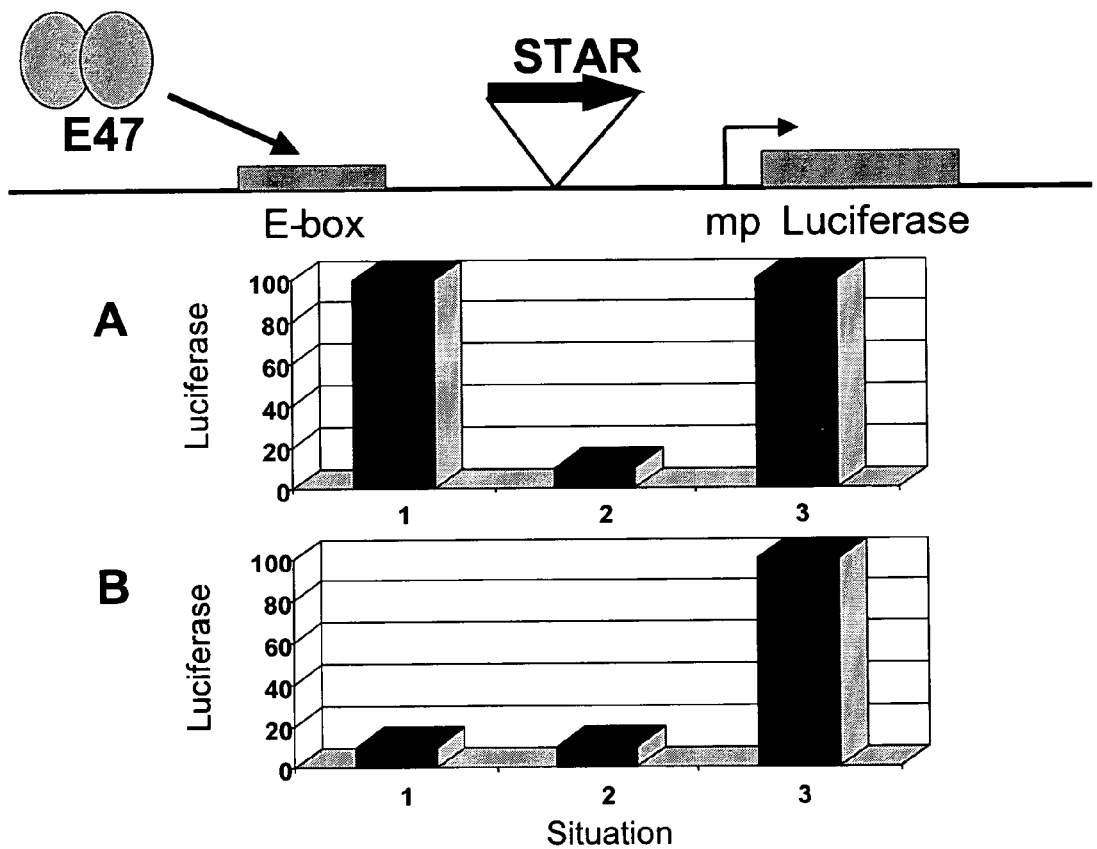
FIG. 16. Enhancer-blocking and enhancer assays. The luciferase expression vectors used for testing STARs for enhancer-blocking and enhancer activity are shown schematically. The E-box binding site for the E47 enhancer protein is upstream of a cloning site for STAR elements. Downstream of the STAR cloning site is the luciferase gene under control of a human alkaline phosphatase minimal promoter (mp). The histograms indicate the expected outcomes for the three possible experimental situations (see text). Panel A: Enhancer-blocking assay. Panel B: Enhancer assay.

The enhancer-blocking assay and the enhancer assay are methodologically and conceptually similar. The assays are shown schematically in FIG. 16. The ability of STAR elements to block enhancers is performed using the E47/E-box enhancer system. The E47 protein is able to activate transcription by promoters when it is bound to an E-box DNA sequence located in the vicinity of those promoters (Quong et al., 2002). E47 is normally involved in regulation of B and T lymphocyte differentiation (Quong et al., 2002), but it is able to function in diverse cell types when expressed ectopically (Petersson et al., 2002). The E-box is a palindromic DNA sequence, CANNTG (Knofler et al., 2002). In the enhancer-blocking assay, an E-box is placed upstream of a luciferase reporter gene (including a minimal promoter) in an expression vector. A cloning site for STAR elements is placed between the E-box and the promoter. The E47 protein is encoded on a second plasmid. The assay is performed by transfecting both the E47 plasmid and the luciferase expression vector into cells; the E47 protein is expressed and binds to the E-box, and the E47/E-box complex is able to act as an enhancer. When the luciferase expression vector does not contain a STAR element, the E47/E-box complex enhances luciferase expression (FIG. 16A, situation 1). When STAR elements are inserted between the E-box and the promoter, their ability to block the enhancer is demonstrated by reduced expression of luciferase activity (FIG. 16A, situation 2); if STARs cannot block enhancers, luciferase expression is activated (FIG. 16A, situation 3).

The ability of STAR elements to act as enhancers utilizes the same luciferase expression vector. In the absence of E47, the E-box itself does not affect transcription. Instead, enhancer behavior by STAR elements will result in activation of luciferase transcription. The assay is performed by transfecting the luciferase expression vector without the E47 plasmid. When the expression vector does not contain STAR elements, luciferase expression is low (FIG. 16B, situation 1). If STAR elements do not have enhancer properties, luciferase expression is low when a STAR element is present in the vector (FIG. 16B, situation 2). If STAR elements do have enhancer properties, luciferase expression will be activated in the STAR-containing vectors (FIG. 16B, situation 3).

Materials and Methods: The luciferase expression vector was constructed by inserting the E-box and a human alkaline phosphatase minimal promoter from plasmid mu-E5+E2x6-cat(x) (Ruezinsky et al., 1991) upstream of the luciferase gene in plasmid pGL3-basic (Promega E1751), to create pGL3-E-box-luciferase (gift of W. Romanow). The E47 expression plasmid contains the E47 open reading frame under control of a beta-actin promoter in the pHBAPr-1-neo plasmid; E47 in constitutively expressed from this plasmid (gift of W. Romanow).

STAR elements 1, 2, 3, 6, 10, 11, 18, and 27 have been cloned into the luciferase expression vector. Clones containing the Drosophila scs element and the chicken beta-globin HS4-6x core ("HS4") element have been included as positive controls (they are known to block enhancers, and to have no intrinsic enhancer properties (Chung et al., 1993, Kellum & Schedl, 1992)), and the empty luciferase expression vector has been included as a negative control. All assays were performed using the U-2 OS cell line. In the enhancer-blocking assay, the E47 plasmid was co-transfected with the luciferase expression vectors (empty vector, or containing STAR or positive-control elements). In the enhancer assay, the E47 plasmid was co-transfected with STARless luciferase expression vector as a positive control for enhancer activity; all other samples received a mock plasmid during co-transfection. The transiently transfected cells were assayed for luciferase activity 48 hours after plasmid transfection (supra). The luciferase activity expressed from a plasmid containing no E-box or STAR/control elements was subtracted, and the luciferase activities were normalized to protein content as described (supra).

Figure 17:
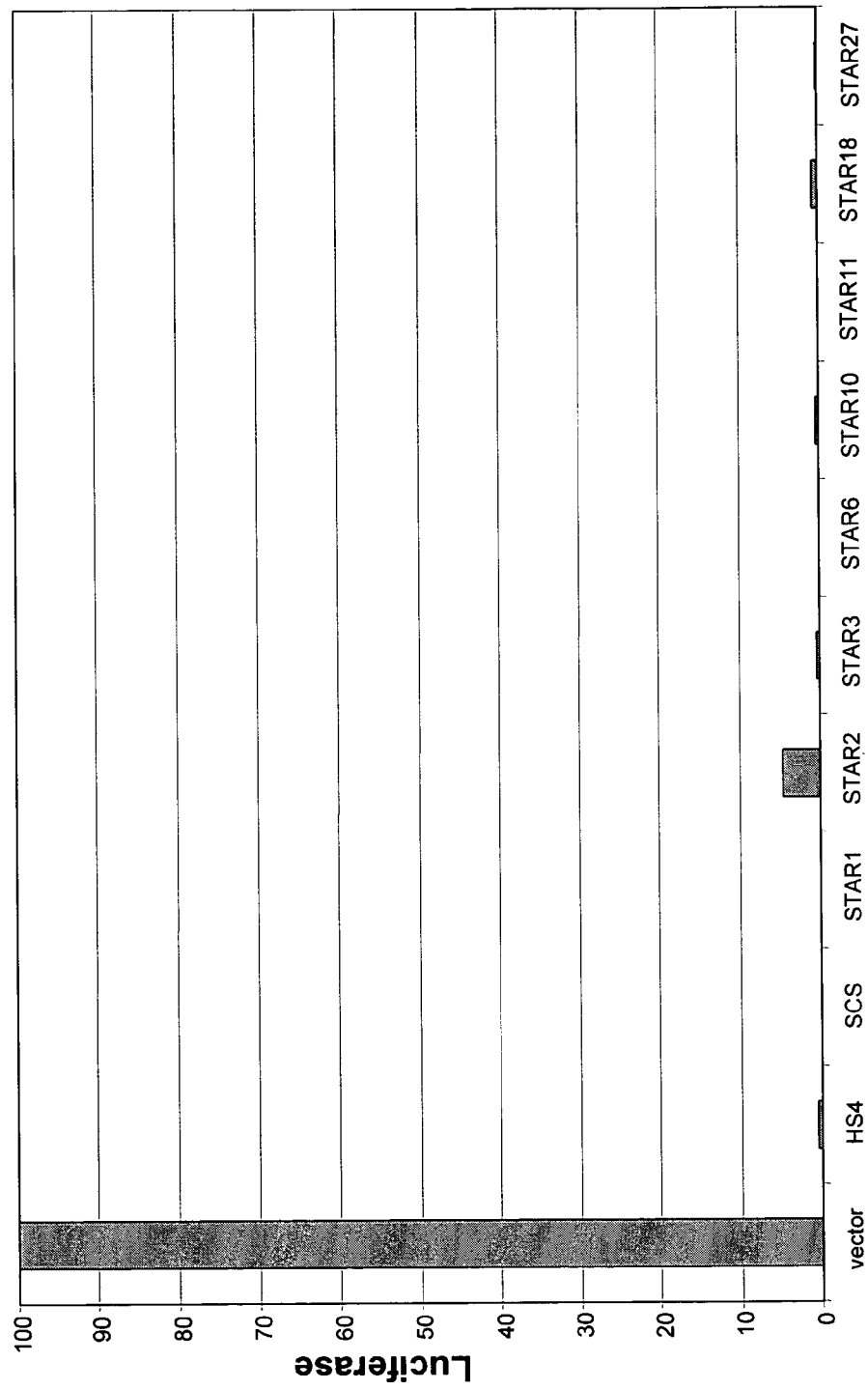
FIG. 17. Enhancer-blocking assay. Luciferase expression from a minimal promoter is activated by the E47/E-box enhancer in the empty vector (vector). Insertion of enhancer-blockers (scs, HS4) or STAR elements (STAR elements 1, 2, 3, 6, 10, 11, 18, and 27) block luciferase activation by the E47/E-box enhancer.

Results: FIG. 17 shows the results of the enhancer-blocking assay. In the absence of STAR elements (or the known enhancer-blocking elements scs and HS4), the E47/E-box enhancer complex activates expression of luciferase ("vector"); this enhanced level of expression has been normalized to 100. Enhancer activity is blocked by all STAR elements tested. Enhancer activity is also blocked by the HS4 and scs elements, as expected (Bell et al., 2001, Gerasimova & Corces, 2001). These results demonstrate that in addition to their ability to block the spreading of transcriptional silencing (negative influences), STAR elements are able to block the action of enhancers (positive influences).

Figure 18:
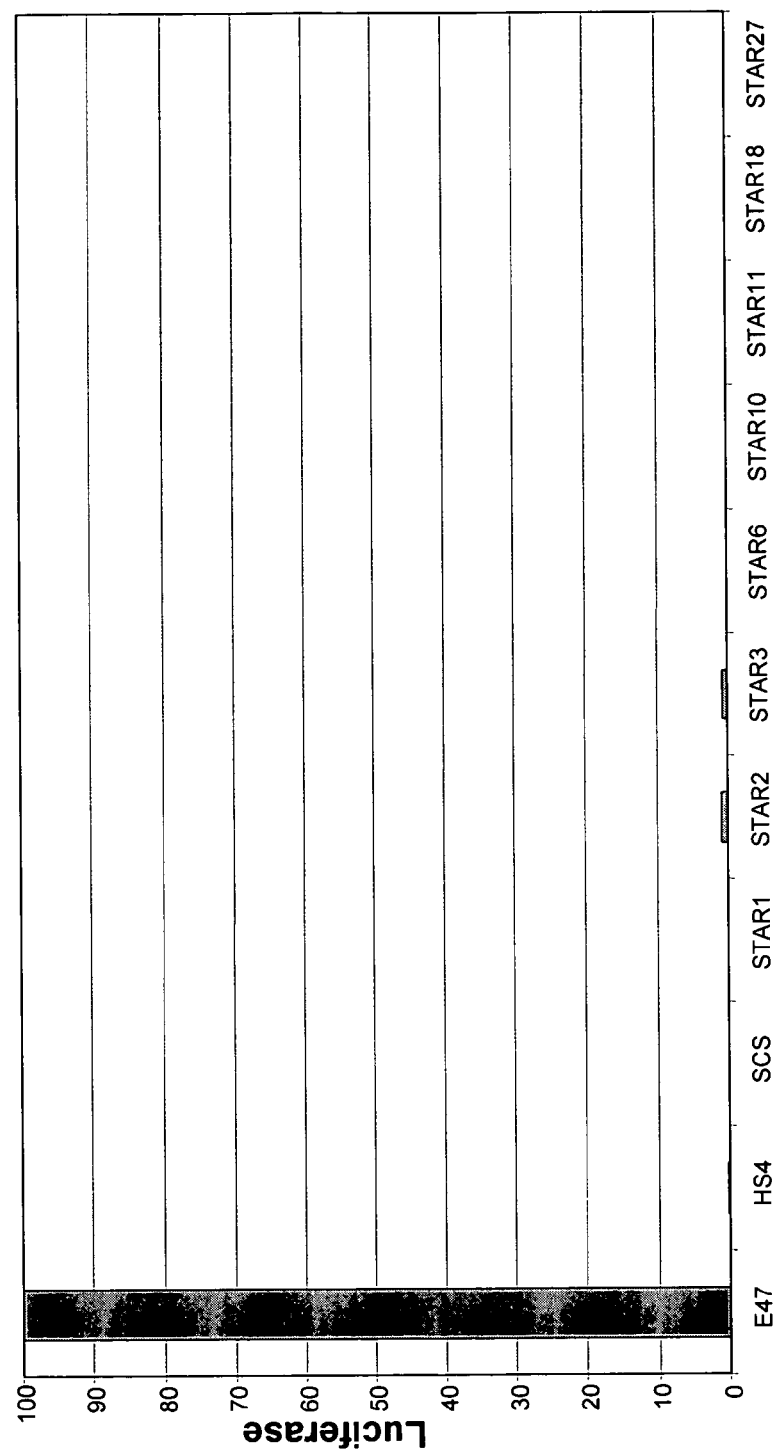
FIG. 18. Enhancer assay. Luciferase expression from a minimal promoter is activated by the E47/E-box enhancer in the empty vector (E47). Insertion of the scs and HS4 elements or various STAR elements (STARs 1, 2, 3, 6, 10, 11, 18, and 27) do not activate transcription of the reporter gene.

FIG. 18 shows the results of the enhancer assay. The level of luciferase expression due to enhancement by the E47/E-box complex is set at 100 ("E47"). By comparison, none of the STAR elements bring about significant activation of luciferase expression. As expected, the scs and HS4 elements also do not bring about activation of the reporter gene. Therefore it is concluded that at least the tested STAR elements do not possess enhancer properties.

Example 20

STAR Elements are Conserved Between Mouse and Human

BLAT analysis of the STAR DNA sequence against the human genome database (genome.ucsc.edu/cgi-bin/hgGateway) reveals that some of these sequences have high sequence conservation with other regions of the human genome. These duplicated regions are candidate STAR elements; if they do show STAR activity, they would be considered paralogs of the cloned STARs (two genes or genetic elements are the to be paralogous if they are derived from a duplication event (Li, 1997)).

BLAST analysis of the human STARs against the mouse genome (www.ensembl.org/Mus_musculus/blastview) also reveals regions of high sequence conservation between mouse and human. This sequence conservation has been shown for fragments of 15 out of the 65 human STAR elements. The conservation ranges from 64% to 89%, over lengths of 141 base pairs to 909 base pairs (Table 7). These degrees of sequence conservation are remarkable and suggest that these DNA sequences may confer STAR activity within the mouse genome as well. Some of the sequences from the mouse and human genomes in Table 7 could be strictly defined as orthologs (two genes or genetic elements are the to be orthologous if they are derived from a speciation event (Li, 1997)). For example, STAR6 is between the SLC8A1 and HAAO genes in both the human and mouse genomes. In other cases, a cloned human STAR has a paralog within the human genome, and its ortholog has been identified in the mouse genome. For example, STAR3a is a fragment of the 15q11.2 region of human chromosome 15. This region is 96.9% identical (paralogous) with a DNA fragment at 5q33.3 on human chromosome 5, which is near the IL12B interleukin gene. These human DNAs share approximately 80% identity with a fragment of the 11B2 region on mouse chromosome 11. The 11B2 fragment is also near the (mouse) IL12B interleukin gene. Therefore STAR3a and the mouse 11B2 fragment can be strictly defined as paralogs.

In order to test the hypothesis that STAR activity is shared between regions of high sequence conservation in the mouse and human genome, one of the human STARs with a conserved sequence in mouse, STAR18, has been analyzed in greater detail. The sequence conservation in the mouse genome detected with the original STAR1 8 clone extends leftward on human chromosome 2 for about 500 base pairs (FIG. 19; left and right relate to the standard description of the arms of chromosome 2). In this example we examine whether the region of sequence conservation defines a "naturally occurring" STAR element in human that is more extensive in length than the original clone. We also examine whether the STAR function of this STAR element is conserved between mouse and human.

Materials and Methods: The region of mouse/human sequence conservation around STAR 18 was recovered from human BAC clone RP11-387A1 by PCR amplification, in three fragments: the entire region (primers E93 and E94), the leftward half (primers E93 and E92), and the rightward half (primers E57 and E94). The corresponding fragments from the homologous mouse region were recovered from BAC clone RP23-400H17 in the same fashion (primers E95 and E98, E95 and E96, and E97 and E98, respectively). All fragments were cloned into the pSelect vector and transfected into a U-2 OS/Tet-Off/LexA-HP1 cell line (supra). Following transfection, hygromycin selection was carried out to select for transfected cells. The LexA-HP1 protein was induced by lowering the doxycycline concentration, and the ability of the transfected cells to withstand the antibiotic Zeocin (a measure of STAR activity) was assessed. by monitoring cell growth.

Figure 19:
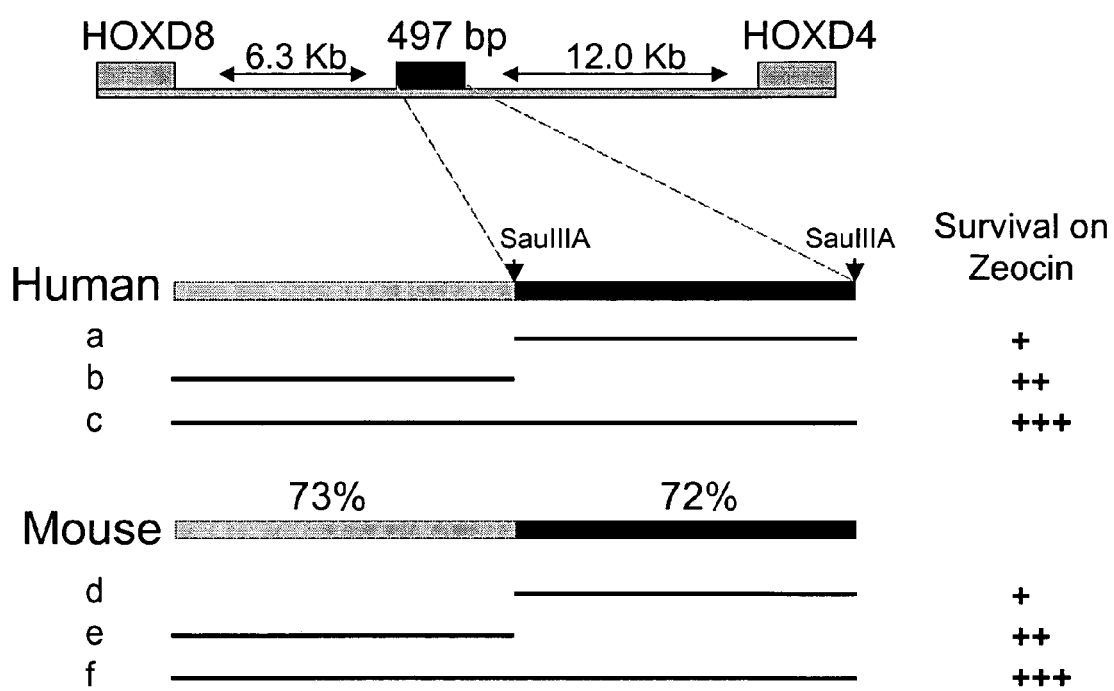
FIG. 19. STAR18 sequence conservation between mouse and human. The region of the human genome containing 497 base pair STAR18 is shown (black boxes); the element occurs between the HOXD8 and HOXD4 homeobox genes on human chromosome 2. It is aligned with a region in mouse chromosome 2 that shares 72% sequence identity. The region of human chromosome 2 immediately to the left of STAR18 is also highly conserved with mouse chromosome 2 (73% identity; gray boxes); beyond these region, the identity drops below 60%. The ability of these regions from human and mouse, either separately or in combination, to confer growth on Zeocin is indicated: −, no growth; +, moderate growth; ++, vigorous growth; +++, rapid growth.

Results: The original STAR18 clone was isolated from Sau3AI digested human DNA ligated into the pSelect vector on the basis of its ability to prevent silencing of a Zeocin resistance gene. Alignment of the human STAR18 clone (497 base pairs) with the mouse genome revealed high sequence similarity (72%) between the orthologous human and mouse STAR18 regions. It also uncovered high similarity (73%) in the region extending for 488 base pairs immediately leftwards of the Sau3AI site that defines the left end of the cloned region (FIG. 19). Outside these regions the sequence similarity between human and mouse DNA drops below 60%.

As indicated in FIG. 19, both the human and the mouse STAR18 elements confer survival on Zeocin to host cells expressing the lexA-HP1 repressor protein. The original 497 base pair STAR 18 clone and its mouse ortholog both confer the ability to grow (FIG. 19, a and d). The adjacent 488 base pair regions of high similarity from both genomes also confer the ability to grow, and in fact their growth phenotype is more vigorous than that of the original STAR18 clone (FIG. 19, b and e). When the entire region of sequence similarity was tested, these DNAs from both mouse and human confer growth, and the growth phenotype is more vigorous than the two sub-fragments (FIG. 19, c and f). These results demonstrate that the STAR activity of human STAR18 is conserved in its ortholog from mouse. The high sequence conservation between these orthologous regions is particularly noteworthy because they are not protein-coding sequences, leading to the conclusion that they have some regulatory function that has prevented their evolutionary divergence through mutation.

This analysis demonstrates that cloned STAR elements identified by the original screening program may in some cases represent partial STAR elements, and that analysis of the genomic DNA in which they are embedded can identify sequences with stronger STAR activity.

Example 21

Materials and Methods: Using the genetic screen described in the original patent application, sixty-six (66) STAR elements were initially isolated from human genomic DNA and characterized in detail (Table 5). The screen was performed on gene libraries constructed by Sau3AI digestion of human genomic DNA, either purified from placenta (Clontech 6550-1) or carried in bacterial/P1 (BAC/PAC) artificial chromosomes. The BAC/PAC clones contain genomic DNA from regions of chromosome 1 (clones RP1154H19 and RP3328E19), from the HOX cluster of homeotic genes (clones RP1167F23, RP1170019, and RP11387A1), or from human chromosome 22 (Research Genetics 96010-22). The DNAs were size-fractionated, and the 0.5-2 kb size fraction was ligated into BamHI-digested pSelect vector, by standard techniques (Sambrook et al., 1989). pSelect plasmids containing human genomic DNA that conferred resistance to Zeocin at low doxycycline concentrations were isolated and propagated in *Escherichia coli*. The screens that yielded the STAR elements of Table 5 have assayed approximately 1-2% of the human genome.

The human genomic DNA inserts in these 66 plasmids were sequenced by the dideoxy method (Sanger et al., 1977) using a Beckman CEQ2000 automated DNA sequencer, using the manufacturer's instructions. Briefly, DNA was purified from *E. coli* using OIAPREP® Spin Miniprep and Plasmid Midi Kits (QIAGEN 27106 and 12145, respectively). Cycle sequencing was carried out using custom oligonucleotides corresponding to the pSelect vector (primers D89 and D95, Table 4), in the presence of dye terminators (CEQ Dye Terminator Cycle Sequencing Kit, Beckman 608000). Assembled STAR DNA sequences were located in the human genome (database builds August and December 2001) using BLAT (Basic Local Alignment Tool (Kent, 2002); genome.ucsc.edu/cgi-bin/hgGateway; Table 5). In aggregate, the combined STAR sequences comprise 85.6 kilobase pairs, with an average length of 1.3 kilobase pairs.

The contents of the following references are each incorporated, in their entirety, by this reference.

REFERENCES

Altschul, S. F. and Gish, W. (1996) Local alignment statistics. Methods Enzymol, 266, 460-480.

Altschul, S. F., Gish, W., Miller, W., Myers, E. W. and Lipman, D. J. (1990) Basic local alignment search tool. J Mol Biol, 215, 403-410.

Bell, AC, West, AG, and Felsenfeld, G. (2001) Insulators and boundaries: versatile regulatory elements in the eukaryotic genome Science 291, 447-50.

Bennett et al. (1998) Fusion of green fluorescent protein with the Zeocin-resistance marker allows visual screening and drug selection of transfected eukaryotic cells. Biotechniques, 24, 478-482.

Berger et al. (1988) Secreted placental alkaline phosphatase: a powerful new quantitative indicator of gene expression in eukaryotic cells Gene 66, 1-10.

Bierhuizen et al. (1997) Green fluorescent protein variants as markers of retroviral-mediated gene transfer in primary hematopoietic cells and cell lines. Biochem Biophys Res Commun, 234, 371-375.

Boivin, A, and Dura, J M. (1998) In vivo chromatin accessibility correlates with gene silencing in Drosophila Genetics 150, 1539-49.

Boshart et al. (1985) A very strong enhancer is located upstream of an immediate early gene of human cytomegalovirus Cell 41, 521-30.

Bunker, C. A. and Kingston, R. E. (1994) Transcriptional repression by Drosophila and mammalian Polycomb group proteins in transfected mammalian cells. Mol Cell Biol, 14, 1721-1732.

Cherry et al. (1999) Directed evolution of a fungal peroxidase. Nat Biotechnol, 17, 379-384.

Chung, J H, Whiteley, M, and Felsenfeld, G. (1993) A 5' element of the chicken beta-globin domain serves as an insulator in human erythroid cells and protects against position effect in Drosophila Cell 74, 505-14.

Deuschle, U, Meyer, W K, and Thiesen, H J. (1995) Tetracycline-reversible silencing of eukaryotic promoters Mol Cell Biol 15, 1907-14.

Doll, R. F., Crandall, J. E., Dyer, C. A., Aucoin, J. M. and Smith, F. I. (1996) Comparison of promoter strengths on gene delivery into mammalian brain cells using AAV vectors.
Gene Ther, 3, 437-447.

Feng et al. (1999) Site-specific chromosomal integration in mammalian cells: highly efficient CRE recombinase-mediated cassette exchange. J Mol Biol, 292, 779-785.

Foecking, M K, and Hofstetter, H. (1986) Powerful and versatile enhancer-promoter unit for mammalian expression vectors Gene 45, 101-5.

Garrick, D, Fiering, S, Martin, D I, and Whitelaw, E. (1998) Repeat-induced gene silencing in mammals Nat Genet 18, 56-9.

Gaszner, M., Vazquez, J. and Schedl, P. (1999) The Zw5 protein, a component of the scs chromatin domain boundary, is able to block enhancer-promoter interaction. Genes Dev, 13, 2098-2107.

Gerasimova, T. I. and Corces, V. G. (1998) Polycomb and trithorax group proteins mediate the function of a chromatin insulator. Cell, 92, 511-521.

Gerasimova, T I, and Corces, V G. (2001) Chromatin insulators and boundaries: effects on transcription and nuclear organization Annu Rev Genet 35, 193-208.

Gossen, M. and Bujard, H. (1992) Tight control of gene expression in mammalian cells by tetracycline-responsive promoters. Proc Natl Acad Sci U S A, 89, 5547-5551.

Graham, F. L. and van der E b, A. J. (1973) Transformation of rat cells by DNA of human adenovirus 5. Virology, 54, 536-539.

Heldin et al. (1986) A human osteosarcoma cell line secretes a growth factor structurally related to a homodimer of PDGF A-chains. Nature, 319, 511-514.

Henke, E. and Bornscheuer, U. T. (1999) Directed evolution of an esterase from Pseudomonas fluorescens. Random mutagenesis by error-prone PCR or a mutator strain and identification of mutants showing enhanced enantioselectivity by a resorufin-based fluorescence assay. Biol Chem, 380, 1029-1033.

Henthom et al. (1988) Expression of a human placental alkaline phosphatase gene in transfected cells: use as a reporter for studies of gene expression Proc Natl Acad Sci U S A 85, 6342-6.

Higgins, D. G., Thompson, J. D. and Gibson, T. J. (1996) Using CLUSTAL for multiple sequence alignments. Methods Enzymol, 266, 383-402.

Himes, S. R. and Shannon, M. F. (2000) Assays for transcriptional activity based on the luciferase reporter gene. Methods Mol Biol, 130, 165-174.

Izumi, M, and Gilbert, D M. (1999) Homogeneous tetracycline-regulatable gene expression in mammalian fibroblasts J Cell Biochem 76, 280-9.

Jung, R., Soondrum, K. and Neumaier, M. (2000) Quantitative PCR. Clin Chem Lab Med, 38, 833-836.

Kain, S R. (1997) Use of secreted alkaline phosphatase as a reporter of gene expression in mammalian cells Methods Mol Biol 63, 49-60.

Kao, F. T. and Puck, T. T. (1968) Genetics of somatic mammalian cells, VII. Induction and isolation of nutritional mutants in Chinese hamster cells. Proc Natl Acad Sci U S A, 60, 1275-81.

Kellum, R. and Schedl, P. (1992) A group of scs elements function as domain boundaries in an enhancer-blocking assay. Mol Cell Biol, 12, 2424-2431.

Kent, W J. (2002) BLAT—the BLAST-like alignment tool Genome Res 12, 656-64.

Knofler et al. (2002) Human Hand1 basic helix-loop-helix (bHLH) protein: extra-embryonic expression pattern, interaction partners and identification of its transcriptional repressor domains Biochem J 361, 641-51.

Li, W-H (1997) Molecular Evolution, Sinauer Associates, Sunderland M A., Meinke, D W, Cherry, J M, Dean, C, Rounsley, S D, and Koornneef, M. (1998) Arabidopsis thaliana: a model plant for genome analysis Science 282, 662, 679-82.

Litt, M. D., Simpson, M., Recillas-Targa, F., Prioleau, M. N. and Felsenfeld, G. (2001) Transitions in histone acetylation reveal boundaries of three separately regulated neighboring loci. EMBO J, 20, 2224-2235.

Morgenstern, J. P. and Land, H. (1990) Advanced mammalian gene transfer: high titre retroviral vectors with multiple drug selection markers and a complementary helper-free packaging cell line. Nucleic Acids Res, 18, 3587-3596.

Nan, X., Javier Campoy, F., and Bird A. (1997) MeCP2 is a transcriptional repressor with abundant binding sites in genomic chromatin. Cell 88, 471-481.

Petersson, K, Ivars, F, and Sigvardsson, M. (2002) The pT alpha promoter and enhancer are direct targets for transactivation by E box-binding proteins Eur J Immunol 32, 911-20.

Pazin, M. J. and Kadonaga, J. T. (1998) Transcriptional and structural analysis of chromatin assembled in vitro. In Gould, H. (ed.) Chromatin: A Practical Approach. Oxford University Press, Oxford, pp. 172-194.

Quong, M W, Romanow, W J, and Murre, C. (2002) E protein function in lymphocyte development Annu Rev Immunol 20, 301-22.

Ruezinsky, D, Beckmann, H, and Kadesch, T. (1991) Modulation of the IgH enhancer's cell type specificity through a genetic switch Genes Dev 5, 29-37.

Saluz, H. P. and Jost, J. P. (1993) Approaches to characterize protein-DNA interactions in vivo.
Crit Rev Eukaryot Gene Expr, 3, 1-29.

Sambrook, J., Fritsch, E. F. and Maniatis, T. (1989) Molecular Cloning: A Laboratory Manual.
Cold Spring Harbor Laboratory Press, Plainview NY.

Sanger, F., Nicklen, S. and Coulson, A. R. (1977) DNA sequencing with chain-terminating inhibitors. Proc Natl Acad Sci U S A, 74, 5463-5467.

Simizu, B., Rhim, J. S. and Wiebenga, N. H. (1967) Characterization of the Tacaribe group of arboviruses. I. Propagation and plaque assay of Tacaribe virus in a line of African green monkey kidney cells (Vero). Proc Soc Exp Biol Med, 125, 119-123.

Smith, R. L., Traul, D. L., Schaack, J., Clayton, G. H., Staley, K. J. and Wilcox, C. L. (2000) Characterization of promoter function and cell-type-specific expression from viral vectors in the nervous system. J Virol, 74, 11254-11261.

Stull, R. A., Hyun, W. C. and Pallavicini, M. G. (2000) Simultaneous flow cytometric analyses of enhanced green and yellow fluorescent proteins and cell surface antigens in doubly transduced immature hematopoietic cell populations. Cytometry, 40, 126-134.

Takada, T., Iida, K., Akasaka, K., Yasue, H., Torii, R., Tsujimoto, G., Taira, M. and Kimura, H. (2000) Evaluation of heterologous insulator function with regard to chromosomal position effect in the mouse blastocyst and fetus. Mol Reprod Dev, 57, 232-237.

Tanaka, S., Livingstone-Zatchej, M. and Thoma, F. (1996) Chromatin structure of the yeast URA3 gene at high resolution provides insight into structure and positioning of nucleosomes in the chromosomal context. J Mol Biol, 257, 919-934.

Thomas, J. O. (1998) Isolation and fractionation of chromatin and linker histones. In Gould, H. (ed.) Chromatin: A Practical Approach. Oxford University Press, Oxford, pp. 1-34.

Umana, P, Jean-Mairet, J, and Bailey, J E. (1999) Tetracycline-regulated overexpression of glycosyltransferases in Chinese hamster ovary cells Biotechnol Bioeng 65, 542-9.

van der Vlag, J., den Blaauwen, J. L., Sewalt, R. G., van Driel, R. and Otte, A. P. (2000) Transcriptional repression mediated by polycomb group proteins and other chromatin-associated repressors is selectively blocked by insulators. J Biol Chem, 275, 697-704.

Wallrath, L. L., Swede, M. J. and Elgin, S. C. R. (1998) Mapping chromatin structure in Drosophila. In Gould, H. (ed.) Chromatin: A Practical Approach. Oxford University Press, Oxford, pp. 59-77.

Weaver, L. S. and Kadan, M. J. (2000) Evaluation of adenoviral vectors by flow cytometry. Methods, 21, 297-312.

Wigler, M, Pellicer, A., Silverstein, S. and Axel, R. (1978). Biochemical transfer of single-copy eukaryotic genes using total cellular DNA as donor. Cell 14, 725-731.

Wigley, P., Becker, C., Beltrame, J., Blake, T., Crocker, L., Harrison, S., Lyons, I., McKenzie, Z., Tearle, R., Crawford, R. and et al. (1994) Site-specific transgene insertion: an approach. Reprod Fertil Dev, 6, 585-588.

Xu, Z. Z., Krougliak, V., Prevec, L., Graham, F. L. and Both, G. W. (1995) Investigation of promoter function in human and animal cells infected with human recombinant adenovirus expressing rotavirus antigen VP7sc. J Gen Virol, 76, 1971-1980.

Yang, T T, Sinai, P, Kitts, P A, and Kain, S R. (1997) Quantification of gene expression with a secreted alkaline phosphatase reporter system Biotechniques 23, 1110-4.

Zink, D, and Paro, R. (1995) Drosophila Polycomb-group regulated chromatin inhibits the accessibility of a transactivator to its target DNA Embo J 14, 5660-71.

TABLE 1

STAR elements improve transgene expression.

| Plasmid | Over-expressing clones, % | Fold over-expression (range) | Number of clones |
|---|---|---|---|
| Empty | 12 | 3-11 | 25 |
| SCS (positive control) | 24 | 3-160 | 21 |
| STAR-6 (SEQ ID NO: 6) | 62 | 2-200 | 26 |
| STAR-3 (SEQ ID NO: 3) | 39 | 5-820 | 23 |
| STAR-8 (SEQ ID NO: 8) | 63 | 7-315 | 19 |
| STAR-4 (SEQ ID NO: 4) | 31 | 25-1500 | 13 |
| STAR-1 (SEQ ID NO: 1) | 57 | 5-80 | 23 |

Expression of the luciferase reporter gene is measured in cell lines containing integrated pSDH plasmids, without ("empty," the negative control) or containing STAR elements (including the positive control element, SCS from *Drosophila*). The mean expression level of the negative control is defined as the reference level, and clones are considered over-expressing if their expression level is >2-fold above the reference level. The percentage of over-expressing clones for each plasmid and the fold over-expression is reported, along with the number of clones analyzed for each plasmid.

TABLE 2

Cloned STAR element.

| Clone | Chromosomal location[1] | Adjacent genes[2] | Repeat sequence |
|---|---|---|---|
| STAR-1 (SEQ ID NO: 1) | N.d. | | |
| STAR-2 (SEQ ID NO: 2) | N.d. | | |
| STAR-3 (SEQ ID NO: 3) | For 5q33.3 Rev 10q22.2 | Chr10 part in Histone. Acetyltransferase gene | |
| STAR-4 (SEQ ID NO: 4) | For 1p31.1 Rev 14q24.1 | No genes within 10 kb Intron of Regulator of G-protein signaling | 83% repetitive LINE2 & LTR ERV_Class1 |
| STAR-5 (SEQ ID NO: 5) | For 3q13.1 Rev 10q22.1* | | |
| STAR-6 (SEQ ID NO: 6) | 2p21 | L 5 kb Unknown putative kinase R 20 kb Microtuble associated protein | 19% SINE (MIR) 29% LINE |
| STAR-7 (SEQ ID NO: 7) | 1q32.2 | | 12% Alu 4% MIR (SINE) LINE1 2.5% L31CR1 11.5% MER1 7% Low complex 2% |
| STAR-8 (SEQ ID NO: 8) | 9q32 | ZFP KRAB box containing Zinc Finger Protein | 35% ERV_ClassI (LTR) 2% simple repeat |
| STAR-9 (SEQ ID NO: 9) | See STAR4 | | |
| STAR-10 (SEQ ID NO: 10) | N.d. | | |
| STAR-11 (SEQ ID NO: 11) | 2p25.1 | R 15 kb unknown DNA binding protein inhibitor (Myc type) | 12% Alu (SINE) 26% MaLRs (LINE) |
| STAR-12 (SEQ ID NO: 12) | 5q35.3 | R 15 kb unknown ADAM TS2 family metallo proteinase | 3% Low complexity |
| STAR-13 (SEQ ID NO: 13) | See STAR4 and 9 | | |
| STAR-14 (SEQ ID NO: 14) | F N.d. R 20q13.33 | | |
| STAR-15 (SEQ ID NO: 15) | 1p36.36 | L 6 kb Voltage-gated K channel subunit R 4 kb unknown | 14% LTR (MaLRs) |
| STAR-16 (SEQ ID NO: 16) | F 8p23.1 R 8p22 etc. | | No repeat on sequenced parts |

TABLE 2-continued

Cloned STAR element.

| Clone | Chromosomal location[1] | Adjacent genes[2] | Repeat sequence |
|---|---|---|---|
| STAR-17 (SEQ ID NO: 17) | 2q31.1 | L 6 kb BTEB1 transcription factor<br>R 40 kb HNRNP | 10% simple and low complexity |

[1]Chromosomal location is determined by BLAST search of DNA sequence data from the STAR clones against the human genome database. The location is given according to standard nomenclature referring to the cytogenetic ideogram of each chromosome; e.g., 1p2.3 is the third cytogenetic sub-band of the second cytogenetic band of the short arm of chromosome 1 (www.ncbi.nlm.nih.gov/Class/MLACourse/Genetics/chrombanding.html). F, forward sequencing reaction result; R, reverse sequencing reaction result. N.d., not yet determined.
[2]Based on Human Genome Map View Build 22 (www.ncbi.nlm.nih.gov/cgi-bin/Entrez/hum_srch?chr=hum_chr.inf&query April 2001). L, left; R, right.
*Position ambiguous, several hits

TABLE 3

Sequence of various STAR elements in one strand (forward) or the opposite strand (reverse). (SEQ ID NOs: 125-134).

| Sequence |
|---|
| STAR3 forward (SEQ ID NO:125) |
| STAR3 reverse (SEQ ID NO:126) |
| STAR4 forward (SEQ ID NO:127) |
| STAR4 reverse (SEQ ID NO:128) |
| STAR6 forward (SEQ ID NO:129) |
| STAR6 reverse (SEQ ID NO:130) |
| STAR8 forward (SEQ ID NO:131) |
| STAR8 reverse (SEQ ID NO:132) |
| STAR18 forward (SEQ ID NO:133) |
| STAR18 reverse (SEQ ID NO:134) |

TABLE 4

Oligonucleotides used for polymerase chain reactions (PCR primers) or DNA mutagenesis (SEQ ID NOs: 141-183).

| Number | Sequence |
|---|---|
| C65 | (SEQ ID NO:141) |
| C66 | (SEQ ID NO:142) |
| C67 | (SEQ ID NO:143) |
| C68 | (SEQ ID NO:144) |
| C81 | (SEQ ID NO:145) |
| C82 | (SEQ ID NO:146) |
| C85 | (SEQ ID NO:147) |
| D30 | (SEQ ID NO:148) |
| D41 | (SEQ ID NO:149) |
| D42 | (SEQ ID NO:150) |
| D51 | (SEQ ID NO:151) |
| D89 | (SEQ ID NO:152) |
| D90 | (SEQ ID NO:153) |
| D91 | (SEQ ID NO:154) |
| D93 | (SEQ ID NO:155) |
| D94 | (SEQ ID NO:156) |
| D95 | (SEQ ID NO:157) |
| E12 | (SEQ ID NO:158) |
| E13 | (SEQ ID NO:159) |
| E14 | (SEQ ID NO:160) |
| E15 | (SEQ ID NO:161) |
| E16 | (SEQ ID NO:162) |
| E17 | (SEQ ID NO:163) |
| E18 | (SEQ ID NO:164) |
| E19 | (SEQ ID NO:165) |
| E20 | (SEQ ID NO:166) |
| E21 | (SEQ ID NO:167) |
| E22 | (SEQ ID NO:168) |
| E23 | (SEQ ID NO:169) |
| E25 | (SEQ ID NO:170) |
| E42 | (SEQ ID NO:171) |
| E57 | (SEQ ID NO:172) |
| E92 | (SEQ ID NO:173) |
| E93 | (SEQ ID NO:174) |
| E94 | (SEQ ID NO:175) |
| E95 | (SEQ ID NO:176) |
| E96 | (SEQ ID NO:177) |
| E97 | (SEQ ID NO:178) |
| E98 | (SEQ ID NO:179) |
| D58 | (SEQ ID NO:180) |
| D80 | (SEQ ID NO:181) |
| D70 | (SEQ ID NO:182) |
| D71 | (SEQ ID NO:183) |

TABLE 5

STAR elements of the invention, including genomic location and length

| STAR | Location[1] | Length[2] |
|---|---|---|
| 1 (SEQ ID NO: 1) | 2q31.1 | 750 |
| 2 (SEQ ID NO: 2) | 7p15.2 | 916 |
| 3[3] (SEQ ID NO: 3) | 15q11.2 and 10q22.2 | 2132 |
| 4 (SEQ ID NO: 4) | 1p31.1 and 14q24.1 | 1625 |
| 5[4] (SEQ ID NO: 5) | 20q13.32 | 1571 |
| 6 (SEQ ID NO: 6) | 2p21 | 1173 |
| 7 (SEQ ID NO: 7) | 1q34 | 2101 |
| 8 (SEQ ID NO: 8) | 9q32 | 1839 |
| 9[4] (SEQ ID NO: 9) | 10p15.3 | 1936 |
| 10 (SEQ ID NO: 10) | Xp11.3 | 1167 |
| 11 (SEQ ID NO: 11) | 2p25.1 | 1377 |
| 12 (SEQ ID NO: 12) | 5q35.3 | 1051 |
| 13[4] (SEQ ID NO: 13) | 9q34.3 | 1291 |
| 14[4] (SEQ ID NO: 14) | 22q11.22 | 732 |
| 15 (SEQ ID NO: 15) | 1p36.31 | 1881 |
| 16 (SEQ ID NO: 16) | 1p21.2 | 1282 |
| 17 (SEQ ID NO: 17) | 2q31.1 | 793 |
| 18 (SEQ ID NO: 18) | 2q31.3 | 497 |
| 19 (SEQ ID NO: 19) | 6p22.1 | 1840 |
| 20 (SEQ ID NO: 20) | 8p13.3 | 780 |
| 21 (SEQ ID NO: 21) | 6q24.2 | 620 |
| 22 (SEQ ID NO: 22) | 2q12.2 | 1380 |
| 23 (SEQ ID NO: 23) | 6p22.1 | 1246 |
| 24 (SEQ ID NO: 24) | 1q21.2 | 948 |
| 25[5] (SEQ ID NO: 25) | 1q21.3 | 1067 |
| 26 (SEQ ID NO: 26) | 1q21.1 | 540 |
| 27 (SEQ ID NO: 27) | 1q23.1 | 1520 |

TABLE 5-continued

STAR elements of the invention, including genomic location and length

| STAR | Location[1] | Length[2] |
|---|---|---|
| 28 (SEQ ID NO: 28) | 22q11.23 | 961 |
| 29 (SEQ ID NO: 29) | 2q13.31 | 2253 |
| 30 (SEQ ID NO: 30) | 22q12.3 | 1851 |
| 31 (SEQ ID NO: 31) | 9q34.11 and 22q11.21 | 1165 |
| 32 (SEQ ID NO: 32) | 21q22.2 | 771 |
| 33 (SEQ ID NO: 33) | 21q22.2 | 1368 |
| 34 (SEQ ID NO: 34) | 9q34.14 | 755 |
| 35 (SEQ ID NO: 35) | 7q22.3 | 1211 |
| 36 (SEQ ID NO: 36) | 21q22.2 | 1712 |
| 37 (SEQ ID NO: 37) | 22q11.23 | 1331 |
| 38 (SEQ ID NO: 38) | 22q11.1 and 22q11.1 | ~1000 |
| 39 (SEQ ID NO: 39) | 22q12.3 | 2331 |
| 40 (SEQ ID NO: 40) | 22q11.21 | 1071 |
| 41 (SEQ ID NO: 41) | 22q11.21 | 1144 |
| 42 (SEQ ID NO: 42) | 22q11.1 | 735 |
| 43 (SEQ ID NO: 43) | 14q24.3 | 1231 |
| 44 (SEQ ID NO: 44) | 22q11.1 | 1591 |
| 45 (SEQ ID NO: 45) | 22q11.21 | 1991 |
| 46 (SEQ ID NO: 46) | 22q11.23 | 1871 |
| 47 (SEQ ID NO: 47) | 22q11.21 | 1082 |
| 48 (SEQ ID NO: 48) | 22q11.22 | 1242 |
| 49 (SEQ ID NO: 49) | Chr 12 random clone, and 3q26.32 | 1015 |
| 50 (SEQ ID NO: 50) | 6p21.31 | 2361 |
| 51 (SEQ ID NO: 51) | 5q21.3 | 2289 |
| 52 (SEQ ID NO. 52) | 7p15.2 | 1200 |
| 53 (SEQ ID NO: 53) | Xp11.3 | 1431 |
| 54 (SEQ ID NO: 54) | 4q21.1 | 981 |
| 55 (SEQ ID NO: 55) | 15q13.1 | 501 |
| 56 (SEQ ID NO: 56) | includes 3p25.3 | 741 |
| 57 (SEQ ID NO: 57) | 4q35.2 | 1371 |
| 58 (SEQ ID NO: 58) | 21q11.2 | 1401 |
| 59 (SEQ ID NO: 59) | 17 random clone | 872 |
| 60 (SEQ ID NO: 60) | 4p16.1 and 6q27 | 2068 |
| 61 (SEQ ID NO: 61) | 7p14.3 and 11q25 | 1482 |
| 62 (SEQ ID NO: 62) | 14q24.3 | 1011 |
| 63 (SEQ ID NO: 63) | 22q13.3 | 1421 |
| 64 (SEQ ID NO: 64) | 17q11.2 | 1414 |
| 65 (SEQ ID NO: 65) | 7q21.11 = 28.4 | 1310 |
| 66 (SEQ ID NO: 66) | 20q13.33 and 6q14.1 | ~2800 |

[1]Chromosomal location is determined by BLAST search of DNA sequence data from the STAR elements against the human genome database. The location is given according to standard nomenclature referring to the cytogenetic ideogram of each chromosome; e.g., 1p2.3 is the third cytogenetic sub-band of the second cytogenetic band of the short arm of chromosome 1 (www.ncbi.nlm.nih.gov/Class/MLACourse/Genetics/chrombanding.html). In cases where the forward and reverse sequencing reaction identified DNAs from different genomic loci, both loci are shown.
[2]Precise lengths are determined by DNA sequence analysis; approximate lengths are determined by restriction mapping.
[3]Sequence and location of STAR3 has been refined since assembly of Tables 2 and 4.
[4]The STARs with these numbers in Tables 2 and 4 have been set aside (hereafter referred to as "oldSTAR5" etc.) and their numbers assigned to the STAR elements shown in the DNA sequence appendix. In the case of oldSTAR5, oldSTAR14, and oldSTAR16, the cloned DNAs were chimeras from more than two chromosomal locations; in the case of oldSTAR9 and oldSTAR13, the cloned DNAs were identical to STAR4.
[5]Identical to Table 3 "STAR18".

TABLE 6

STAR elements convey stability over time on transgene expression[1]

| | Cell Divisions[2] | Luciferase Expression[3] |
|---|---|---|
| STAR6 plus puromycin | 42 | 18,000 |
| | 60 | 23,000 |
| | 84 | 20,000 |
| | 108 | 16,000 |
| STAR6 without puromycin[4] | 84 | 12,000 |
| | 108 | 15,000 |
| | 144 | 12,000 |

[1]Plasmid pSDH-Tet-STAR6 was transfected into U-2 OS cells, and clones were isolated and cultivated in doxycycline-free medium as described in Example 1. Cells were transferred to fresh culture vessels weekly at a dilution of 1:20.
[2]The number of cell divisions is based on the estimation that in one week the culture reaches cell confluence, which represents ~6 cell divisions.
[3]Luciferase was assayed as described in Example 1.
[4]After 60 cell divisions the cells were transferred to two culture vessels; one was supplied with culture medium that contained puromycin, as for the first 60 cell divisions, and the second was supplied with culture medium lacking antibiotic.

TABLE 7

Human STAR elements and their putative mouse orthologs and paralogs

| SEQ: ID | STAR | Human[1] | Mouse[2] | Similarity[3] |
|---|---|---|---|---|
| 1 | 1 | 2q31.1 | 2D | 600 bp 69% |
| 2 | 2 | 7p15.2 | 6B3 | 909 bp 89% |
| 3 | 3a | 5q33.3 | 11B2 | 248 bp 83% |
| 4 | 3b | 10q22.2 | 14B | 1. 363 bp 89% |
| | | | | 2. 163 bp 86% |
| 5 | 6 | 2p21 | 17E4 | 437 bp 78% |
| 6 | 12 | 5q35.3 | 11b1.3 | 796 bp 66% |
| 7 | 13 | 9q34.3 | 2A3 | 753 bp 77% |
| 8 | 18 | 2q31.3 | 2E1 | 497 bp 72% |
| 9 | 36 | 21q22.2 | 16C4 | 166 bp 79% |
| 10 | 40 | 22q11.1 | 6F1 | 1. 270 bp 75% |
| | | | | 2. 309 bp 70% |
| 11 | 50 | 6p21.31 | 17B1 | 1. 451 bp 72% |
| | | | | 2. 188 bp 80% |
| | | | | 3. 142 bp 64% |
| 12 | 52 | 7p15.2 | 6B3 | 1. 846 bp 74% |
| | | | | 2. 195 bp 71% |
| 13 | 53 | Xp11.3 | XA2 | 364 bp 64% |
| 14 | 54 | 4q21.1 | 5E3 | 1. 174 bp 80% |
| | | | | 2. 240 bp 73% |
| | | | | 3. 141 bp 67% |
| | | | | 4. 144 bp 68% |
| 15 | 61a | 7p14.3 | 6B3 | 188 bp 68% |

[1]Cytogenetic location of STAR element in the human genome.
[2]Cytogenetic location of STAR element ortholog in the mouse genome.
[3]Length of region(s) displaying high sequence similarity, and percentage similarity. In some cases more than one block of high similarity occurs; in those cases, each block is described separately. Similarity <60% is not considered significant.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07655441B2). An electronic copy of the "Sequence Listing" will also be available from the USPTO upon request and payment of the fee set forth in 37 CFR 1.19(b)(3).

What is claimed is:

1. A nucleotide construct comprising an expression cassette comprising a promoter operably linked to a nucleic acid sequence of interest, wherein the nucleotide construct comprises the sequence of SEQ ID NO: 45 both upstream and downstream of the expression cassette.

2. The nucleotide construct of claim 1, wherein the nucleic acid sequence of interest is a transgene open reading frame.

3. The nucleotide construct of claim 1, wherein the promoter is an exogenous promoter.

4. The nucleotide construct of claim 1, wherein the promoter is a constitutive promoter.

5. The nucleotide construct of claim 1, wherein the promoter is a viral promoter.

6. The nucleotide construct of claim 1, wherein the promoter is an inducible promoter.

7. The nucleotide construct of claim 1, wherein the promoter is a CMV promoter.

8. The nucleotide construct of claim 1, wherein the promoter is an SV40 promoter.

9. The nucleotide construct of claim 1, wherein all copies of SEQ ID NO: 45 are directed with their 3' ends to the expression cassette.

10. A DNA construct comprising in the following order:
   (i) SEQ ID NO: 45;
   (ii) an expression cassette comprising a promoter operably linked to a nucleic acid sequence of interest; and
   (iii) SEQ ID NO: 45, in opposite orientation as (i).

11. The DNA construct of claim 10, wherein the 3' end of SEQ ID NO: 45 both in (i) and (iii) is directed to the expression cassette.

12. The DNA construct of claim 10, wherein the nucleic acid sequence of interest is a transgene open reading frame.

13. An isolated cell comprising the nucleotide construct of claim 1.

14. An isolated cell comprising the nucleotide construct of claim 2.

15. An isolated cell comprising the DNA construct of claim 10.

16. The cell of claim 13, wherein the nucleotide construct is integrated into the cell's genome.

17. The cell of claim 15, wherein the DNA construct is integrated into the cell's genome.

18. The cell of claim 13, wherein the cell is a Chinese Hamster Ovary (CHO) cell.

19. The cell of claim 15, wherein the cell is a CHO cell.

20. The cell of claim 13, comprising multiple copies of the nucleotide construct.

21. The cell of claim 15, comprising multiple copies of the DNA construct integrated into the cell's genome.

22. A method for expressing a nucleic acid sequence of interest in a cell, said method comprising:
   providing an isolated cell with the nucleotide construct of claim 1, and
   expressing the nucleic acid sequence of interest in the cell.

23. A method for producing a gene product that is encoded by a transgene open reading frame, said method comprising:
   culturing the cell of claim 14 and expressing the transgene open reading frame in the cell.

24. The method according to claim 23, wherein the gene product is a heterologous protein.

25. The method according to claim 23, further comprising: isolating the gene product.

26. A method for producing a gene product in a cell, comprising:
   (a) providing an isolated cell comprising a DNA construct comprising in the following order:
      (i) SEQ ID NO: 45;
      (ii) an expression cassette comprising a promoter operably linked to a nucleic acid sequence encoding the gene product; and
      (iii) SEQ ID NO: 45, in opposite orientation as (i),
   (b) expressing the nucleic acid sequence encoding the gene product in the cell.

* * * * *

UNITED STATES PATENT AND TRADEMARK OFFICE
CERTIFICATE OF CORRECTION

PATENT NO. : 7,655,441 B2 Page 1 of 1
APPLICATION NO. : 11/580760
DATED : February 2, 2010
INVENTOR(S) : Otte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO.         : 7,655,441 B2
APPLICATION NO.    : 11/580760
DATED              : February 2, 2010
INVENTOR(S)        : Arie P. Otte and Arthur L. Kruckeberg Page 1 of 1

It is certified that error appears in the above-identified patent and that said Letters Patent is hereby corrected as shown below:

On the title page:
In ITEM (73) Assignee                            change "Chromagenics B.V.," to --ChromaGenics B.V.,--
In ITEM (56) References Cited
   OTHER PUBLICATIONS, (Page 2)
   1st column, 13th entry, 2nd line     change "postion" to --position--

In the specification:
COLUMN 13   LINE 8                               change "COLLECTION®" to --COLLECTION--
COLUMN 20   LINE 5                               change "Bomscheuer," to --Bornscheuer,--

Signed and Sealed this
Twenty-ninth Day of March, 2011

David J. Kappos
*Director of the United States Patent and Trademark Office*